US 6,627,408 B1

(12) United States Patent
Nislow et al.

(10) Patent No.: US 6,627,408 B1
(45) Date of Patent: *Sep. 30, 2003

(54) ANTIFUNGAL ASSAY

(75) Inventors: Corey E. Nislow, San Francisco, CA (US); Roman Sakowicz, Foster City, CA (US); Christophe Beraud, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/270,085

(22) Filed: Oct. 11, 2002

Related U.S. Application Data

(63) Continuation of application No. 09/723,820, filed on Nov. 28, 2000, now Pat. No. 6,468,760, which is a continuation of application No. 09/541,782, filed on Apr. 3, 2000, now Pat. No. 6,284,480.

(51) Int. Cl.[7] .............. C12Q 1/42; C12Q 1/00; G01N 33/53; C12N 1/00

(52) U.S. Cl. .............. 435/21; 435/4; 435/968; 435/922; 435/942

(58) Field of Search ................. 435/21, 4, 968, 435/922, 942

(56) References Cited

U.S. PATENT DOCUMENTS

| 6,207,403 B1 | 3/2001 | Goldstein et al. ........ 435/21 |
| 6,284,480 B1 * | 9/2001 | Nislow et al. ........... 435/21 |
| 6,468,760 B1 * | 10/2002 | Nislow et al. ........... 435/21 |

FOREIGN PATENT DOCUMENTS

| WO | WO 00/63353 | 10/2000 | ........... C12N/9/16 |

OTHER PUBLICATIONS

Barton et al. (1995), Mol. Biol. Cell, 6:1563–74, "Motor activity and mitotic spindle localization of the Drosophila kinesin–like protein KLP61F".
Cole et al. (1994), J. Biol. Chem. 269:22913–16, "A "slow" homotetrameric kinesin–related motor protein purified from Drosophila embryos".
Drummond et al. (1998), J. Cell Sci. 111:853–65 "Mutations in the bimCbo x of Cut7 indicate divergence of regulation within the bimC family of kinesin related proteins".
Heck et al. (1993), J. Cell Biol. 123:665–79 "The kinesin–like protein KLP6F is essential for mitosis in Drosophila".
Kashina et al. (1996), Nature 379:270–2 "A bipolar kinesin".
Kashina et al. (1997) Biochim. et Biophys. Acta 1357:257–71"The bimC family of kinesins: essential bipolar mitotic motors driving centrosome separation".
Le Guellec et al. (1991), Mol. Cell. Biol. 11:3395–98 "Cloning by differential screening of a Xenopus cDNA that encodes a kinesin–related protein".
Sharp et al. (1999) J. Cell Biol. 144:125–38 "The bipolar kinesin, KLP61F, cross–links microtubules within interpolar microtubule bundles of Drosophila embryonic mitotic spindles".
Whitehead et al. (1998) J. Cell Sci. 111:2551–61 "Expanding the role of HsEg5 within the mitotic and post–mitotic phases of the cell cycle".
US patent application No. 09/314,464, Finer et al., Filed May 18, 1999, Title: Compositions and Assays Utilizing ADP or Phosphate for Detecting Protein Modulators.

* cited by examiner

Primary Examiner—Louise N. Leary
(74) Attorney, Agent, or Firm—Lauren L. Stevens; Beyer Weaver & Thomas, LLP

(57) ABSTRACT

The present invention provides high throughput screening Systems for identifying antifungal compounds. The method can be performed in plurality simultaneously with fluorescence or absorbance readouts.

10 Claims, 18 Drawing Sheets

```
   1 ttttctggcc aacggaacaa cagccgacaa ccacgacatt tgcgacacc gcccctcagc
  61 gagactcatt gcttatttac tgagtttggt cttatgtcca attattgttt ctgtacctaa
 121 ttcctaccgt catttcacat catggccggc cccagcggg ctacttatgg ccttgggacc
 181 aggcgaacga cgacgcgaca gccgacacga cgggcgggtt ctgcgatacc agaacgccag
 241 acatccacag catccccagc tgtatcaaca aaaacggctg ccattagtcg gacgcgcaca
 301 ttaaaatccc cgggcgaacc ggcgagcgtg ctcgcgaagc gaaggagag ggacattgag
 361 cgagaaatca acgaagatac aagcatccat gtcgtcgtac gatgtcgagg ccgtaacgag
 421 cgcgaagtca aggagaacag cggggttgtt ttgcagacag agggcgtgaa gggtaaaact
 481 gtggagttgt caatgggtcc aaatgcagta tcaaacaaga cctacacgtt cgataaagtc
 541 ttctccgcgg cggcagacca aattacggtg tacgaggatg tagttctgcc aattgtcact
 601 gagatgcttg ctggatacaa ttgcaccatc ttcgcatacg acaaaccgg taccggaaag
 661 acatacacga tgtctggaga tatgacggat acattgggta tattatccga caatgctgga
 721 attatccccc gcgttctata ttctctattc gccaaattag ctgatacaga gagtacggta
 781 aaatgctcct ttatcgagct ttacaacgag gaactccgag atttgctctc cgcggaagag
 841 aacccgaagc taaagattta cgacaatgag cagaaaaag gtcatatgag cacactcgta
 901 caaggcatgg aggagacata catcgattcc gcgactgcag gtatcaaact tctccagcaa
 961 ggtagccata agcgtcaagt tgctgcgacc aagtgcaacg acctgagttc acgaagtcat
1021 accgtgttca ccatcacggt gaatatcaag cggactacag agtctgggga ggaatacgtg
1081 tgccctggca agctaaacct ggtcgatctg gctggtagcg agaacattgg gcggagcggt
1141 gcagaaaata agcgtgcaac tgaggctggc ttaattaaca agagtctgct taccccttggc
1201 cgcgtgatca atgccctcgt cgacaagagc caacacattc cctatagaga atctaagctc
1261 acgcgcttac ttcaagattc cctcggcgga cgaaccaaga catgcatcat agctacaatg
1321 tcgcctgcta gaagcaatct agaggagaca atttcaacgc tggactatgc tttcagagcc
1381 aagaatatcc gcaacaagcc gcaaataaac tctaccatgc ctaaaatgac gcttctccgt
1441 gaattcactg ccgaaattga gaaactaaag gcggagttga tcgcgaccag acatcgtaac
1501 ggagtgtaca tgtcagtgga atcttatgag gaaatgaaga tggaaaacga gtcacgaagg
1561 attatcagtg aggagcaacg ggccaaaatc gagtcgatgg agtctagcct tcgccataag
1621 gtccaagagt tactcacttt gacgagcaag ttcaacgacc tgaagaagga caacgacgac
1681 acattggccg ctttatgctc cacaaatgat gtcctccaac agaccgacat tgtcttgcag
1741 aacacccgtg cccagcttga agaggaagag atgctgcgat gtgcgcatga agagactgaa
1801 caccagctcc aggatgtcgg caaaggactt atatcaaccc ttggccaaac cgttgaagat
1861 attaatagcc tacaatcaaa gcttgatcgg aaagccgagt tggacgctac caatgcggaa
1921 ttatggagag cttcctcaac ggaggtttca gatgtcacga agcggattga ccagcgggtt
1981 gaggctttcc agacgcggca tgcaaagctt ctcgaaacca cgtctgtcaa agttaacgag
2041 ttcattgcta cagagatttc taacatcgag aggactcggt cagatctctc cgagtataac
2101 cgctcgcttg atgcggcatg taacaatgcg aaggctgaga catctagtgc tcacgaagac
2161 atgaacaatg tgcttgaaga aatcaaagat ctgcgcgagg aagtcaagtc taaagtagga
2221 gagggactta atggcctctc agctgccgca gcccggatat cggaggaggt tattggtgaa
2281 ttcacccaac ttcacagcca actgcacaca tccttcaata accttggaaa agacctgaaa
2341 tcgatctttg agacgatggc cacgcatctt tcagagcaga agaacgaaat aaacaggcta
2401 cgggccgagc tacagagctc gaaccgccag aacatagaaa cgacgcacaa ggcctccgct
2461 catctcgctc aagcgattga agaagaacac gtcgctgcgg aagcggaacg tgagattta
2521 atgtcacaga tcaaagcgct ggttgaggaa tctcgccaga gcaattcgc ccgcctcagg
2581 gccaagattg acggggtcag gaccgagatt tcagcatcag gggacatgtt agagcaggcc
2641 acaactcagc atgaccgcca gatcgatgag tgggttttca gtctgagca attcgctaag
2701 gatgtcaatg catcgaaaga tgagatcagg acgaagctgc aaaatgattg ggaggcattt
```

FIGURE 1A

```
2761 gatcagcgga attcgacaat ccggaaggca acagaatctg tccataagga gacggtacgc
2821 attgttgacg ttcaagtaga cgacatggga cggcaaatgg aagctctgga cgatttcgtg
2881 gcaaaggcac gatctcagaa tggtcgttac cgtgatgcgc atattgcaac cctggataca
2941 atagccaccg gtgttcgcga ctcctactcc tcgattgagg ggcgggttga aaacttgact
3001 ggccggatga accagttcca acaagaagca acccatcatc atgccactct ggaagaatcc
3061 attgctccgc tatcaaacga tgttaggaag ccccttacgg acttgtcttc cagttttcaa
3121 aatcgttctc tggaggagta tgtcgccact ggtgtcaccc gaagaaacg gaagtacgac
3181 tatatttctg tcttgcctag cacggagtct catgaggtcc tcaagtctcg cctgagaaca
3241 acaaggaga tggaagtcct tccattcaac agcgacgacc agttgtccgg cccttccagc
3301 tctcccggag gttctccgtc gaaaggcttc gtttacaatg acgtcgagga cgaggtagga
3361 actcatgcac caaccgtgac caacgtcaac ccttccaaca ctggacttag ggaagtcgat
3421 gcaaacgtcg ccgcaagacc gctcgtgtat agcacgggcg agaaatccac ggaccaggat
3481 ggttccccag ttgtcagccc ggatagcgcg acagaagcag aagggatgaa cggaccacca
3541 tccaaaaggc gacgctcaaa ttcagttgtt gctgatacta agttgccaaa caagatgctc
3601 gctaggagga tggctggcat gatggagggg agggaaaacg ttccgcctcc tggtatttcc
3661 aatgggcgcc gactgagggg gcgaccttcg ccctgatata ctcttcactc ggacgagttg
3721 atttctcac cgcgaagtat acttataccc tattgctttt ctcgaggtca tgggtttggc
3781 gttctgggaa caatgagatc tgtatcgggc ttttgataga tcgcatatga tacatcgtct
3841 tcgaaagggt tgggtgcttt tttttttttt tgatcggatt tgttgggcat gtgttttgg
3901 gtccggtgtg ggcttctctt ctaccaacat gatgtctggc atccttgaga tacctttttt
3961 gtttagtcgg gctacgattt tgacctagat acttttacct atctccgggg aatt
```

FIGURE 1B

```
MAGPQRATYGLGTRRTTTRQPTRRAGSAIPERQTSTASPAVSTK
TAAISRTRTLKSPGEPASVLAKRKERDIEREINEDTSIHVVVRCRGRNEREVKENSGV
VLQTEGVKGKTVELSMGPNAVSNKTYTFDKVFSAAADQITVYEDVVLPIVTEMLAGYN
CTIFAYGQTGTGKTYTMSGDMTDTLGILSDNAGIIPRVLYSLFAKLADTESTVKCSFI
ELYNEELRDLLSAEENPKLKIYDNEQKKGHMSTLVQGMEETYIDSATAGIKLLQQGSH
KRQVAATKCNDLSSRSHTVFTITVNIKRTTESGEEYVCPGKLNLVDLAGSENIGRSGA
ENKRATEAGLINKSLLTLGRVINALVDKSQHIPYRESKLTRLLQDSLGGRTKTCIIAT
MSPARSNLEETISTLDYAFRAKNIRNKPQINSTMPKMTLLREFTAEIEKLKAELIATR
HRNGVYMSVESYEEMKMENESRRIISEEQRAKIESMESSLRHKVQELLTLTSKFNDLK
KDNDDTLAALCSTNDVLQQTDIVLQNTRAQLEEEEMLRCAHEETEHQLQDVGKGLIST
LGQTVEDINSLQSKLDRKAELDATNAELWRASSTEVSDVTKRIDQRVEAFQTRHAKLL
ETTSVKVNEFIATEISNIERTRSDLSEYNRSLDAACNNAKAETSSAHEDMNNVLEEIK
DLREEVKSKVGEGLNGLSAAAARISEEVIGEFTQLHSQLHTSFNNLGKDLKSIFETMA
THLSEQKNEINRLRAELQSSNRQNIETTHKASAHLAQAIEEEHVAAEAEREILMSQIK
ALVEESRQKQFARLRAKIDGVRTEISASGDMLEQATTQHDRQIDEWVFKSEQFAKDVN
ASKDEIRTKLQNDWEAFDQRNSTIRKATESVHKETVRIVDVQVDDMGRQMEALDDFVA
KARSQNGRYRDAHIATLDTIATGVRDSYSSIEGRVENLTGRMNQFQQEATHHHATLEE
SIAPLSNDVRKPLTDLSSSFQNRSLEEYVATGVTPKKRKYDYISVLPSTESHEVLKSR
LRTTKEMEVLPFNSDDQLSGPSSSPGGSPSKGFVYNDVEDEVGTHAPTVTNVNPSNTG
LREVDANVAARPLVYSTGEKSTDQDGSPVVSPDSATEAEGMNGPPSKRRRSNSVVADT
KLPNKMLARRMAGMMEGRENVPPPGISNGRRLRGRPSP
```

FIGURE 2

```
   1 aagcaagaat tgaacatgga tgaattcatt ggatcaaaga ccgatttaat caaagatcaa
  61 gtgagagata ttcttgataa attgaatatt atttaattct tcatttagaa aaatttcagc
 121 tgctttttt ttctttttc tttccttagg cgtctcgagg ttacaagtcg gagtccctct
 181 tcactatcgt ttgtccactt ttttatatc cccattattt tcaatctgaa tttcattttt
 241 tttttttaat tcatgaaatt tatatgtccc acgtattact acatatttgc gttttaatt
 301 aaataaataa ctgttacttt tattatatct tatttgcaga tcacttatct gatcaaatgt
 361 tttcgttttc gtgtgtggtg acgatgtatt aggtacgcga aataaacaaa acaaacaaac
 421 aaggccgcaa caataacatc atctaaagac ttcctttgtg acccgcttct caacagcggg
 481 tgtagaactt atggtatggc cagaaagtaa cgttgagtat agatacagaa gcaagcaatt
 541 caaaggaaaa agtaataaaa agtatataaa agcgcaaaaa atacaacaag aaagaatttg
 601 tttgatgcca gcggaaaacc aaaatacggg tcaagataga agctccaaca gcatcagtaa
 661 aaatggcaac tctcaggttg gatgtcacac tgttcctaat gaggaactga acatcactgt
 721 agctgtgcga tgcagaggaa ggaatgaaag ggaaattagt atgaaaagct ccgttgtggt
 781 aaatgttcca gatattacag gttctaaaga aatttccatt aacacgacgg gagataccgg
 841 tataactgct caaatgaatg ccaagagata cacagtggac aaagtcttcg gtcccggcgc
 901 ttcccaggat ctaatttttg atgaagtggc gggcccatta ttccaggatt tcattaaagg
 961 ttacaattgc accgtactgg tatatggtat gacgtcaaca ggtaaaacat atacaatgac
1021 gggcgacgaa aagttatata atggtgaatt gagcgatgca gcaggaatta taccgagggt
1081 tcttttgaag ttgtttgaca cattggaact acaacagaac gattacgtag taaaatgttc
1141 gttcattgaa ctctacaacg aagaattgaa ggacctcttg gacagcaata gcaacggctc
1201 tagtaatact ggctttgacg gccaatttat gaaaaaattg aggatttttg cttcaagcac
1261 agcaaataat accactagca acagtgctag tagttccagg agtaattcta ggaacagttc
1321 tccgaggtca ttaaatgatc taacacctaa agctgctcta ttaagaaaaa ggttaaggac
1381 aaaatcactg ccgaatacca tcaagcaaca gtatcaacaa caacaggcag tgaattccag
1441 gaacaactct tcctctaact ctggctctac cactaataat gcttctagta acaccaacac
1501 aaataacggt caaagaagtt cgatggctcc aaatgaccaa actaatggta tatacatcca
1561 gaatttgcaa gaatttcaca taacaaatgc tatggagggg ctaaacctat tacaaaaagg
1621 cttaaagcat aggcaagtag cgtccactaa aatgaacgat ttttccagta gatctcatac
1681 catttttaca atcactttgt ataagaagca tcaggatgaa ctatttagaa tttccaaaat
1741 gaatcttgtg gatttagctg gttcagaaaa catcaacaga tccggagcat taaatcaacg
1801 tgccaaagaa gctggttcaa tcaaccaaag tctattgacg ctgggcaggg tcataaacgc
1861 actcgtagat aaaagcggcc atataccttt ccgtgaatcg aaattgaccc gcctgcttca
1921 agattccctg ggtggtaata cgaaaaccgc actaattgct actatatcgc ctgcaaaggt
1981 aacttctgaa gaaacctgca gtacattaga gtatgcttcg aaggctaaaa acattaagaa
2041 caagccgcaa ctgggttcat ttataatgaa ggatatttg gttaaaaata taactatgga
2101 attagcaaag attaaatccg atttactctc tacaaagtcc aaagaaggaa tatatatgag
2161 ccaagatcac tacaaaaatt tgaacagtga tttagaaagt tataaaaatg aagttcaaga
2221 atgtaaaaga gaaattgaaa gtttgacatc gaaaaatgca ttgctagtaa aagataaatt
2281 gaagtcaaaa gaaactattc aatctcaaaa ttgccaaata gaatcattga aaactaccat
2341 agatcattta agggcacaac tagataaaca gcataaaact gaaattgaaa tatccgattt
2401 taataacaaa ctacagaagt tgactgaggt aatgcaaatg ccctacatg attacaaaaa
2461 aagagaactt gaccttaatc aaaagtttga aatgcatatt actaaagaaa ttaaaaaatt
2521 gaaatctaca ctgtttttac aattaaacac tatgcaacag gaaagtattc ttcaagagac
2581 taatatccaa ccaaatcttg atatgatcaa aaatgaagta ctgactctta tgagaaccat
2641 gcaagaaaaa gctgaactaa tgtacaaaga ctgtgtgaag aaaatttaa acgaatctcc
2701 taaattcttc aatgttgtta ttgagaaaat cgacataata agagtagatt tccaaaaatt
```

FIGURE 3A

```
2761 ttataaaaat atagccgaga atctttctga tattagcgaa gaaaataaca acatgaaaca
2821 gtacttaaaa aaccattttt tcaagaataa ccatcaagaa ttactgaatc gtcatgtgga
2881 ttctacttat gaaaatattg agaagagaac aaacgagttt gttgagaact ttaaaaaggt
2941 cctaaatgac caccttgacg aaaataaaaa actaataatg cacaatctga caactgcaac
3001 cagcgcggtt attgatcaag aaatggatct gtttgaaccc aagcgcgtta atgggaaaa
3061 ttcatttgat ctgataaatg attgtgactc catgaataac gaattctata atagcatggc
3121 agcgacgcta tcgcaaatca agagtactgt tgatacatca tcaaattcga tgaatgagtc
3181 tatttcagtc atgaaaggac aagtggaaga atcggagaac gctatatccc ttttgaagaa
3241 caataccaaa tttaatgatc aatttgagca gcttattaac aagcataaca tgttgaaaga
3301 taacattaaa aattcgataa catcaacaca ctctcatata actaatgtgg atgatatcta
3361 taatacgatt gaaaacataa tgaaaaacta tggtaacaag gaaaacgcta ccaaagacga
3421 aatgatcgag aacatattga aggaaatacc aaatctaagt aagaaaatgc cgttaaggtt
3481 atcaaacata aatagcaatt cagtgcaaag tgtaatatcg cccaaaaagc atgcaattga
3541 agatgaaaac aaatccagtg aaaatgtgga caatgagggc tcgagaaaaa tgttaaagat
3601 tgaatagttg atattgcctt tcagtcgaat atatattcaa actagtggtt aataaaaaca
3661 aagtatgtaa agaatactca gttattcatt agaaggcaag acagaagaga agggtgtgaa
3721 accacctcta ccaaacacac caagagatga acctaaatca aatttttcaca gagctaacta
3781 tataaacgtt tggattcgtg tgtactatct ttatttacgg aaataagttg taatattaaa
3841 aaaaaaaaaa aacattttga tggacaatga atttctctaa tttt
```

FIGURE 3B

MVWPESNVEYRYRSKQFKGKSNKKYIKAQKIQQERICLMPAENQ
NTGQDRSSNSISKNGNSQVGCHTVPNEELNITVAVRCRGRNEREISMKSSVVVNVPDI
TGSKEISINTTGDTGITAQMNAKRYTVDKVFGPGASQDLIFDEVAGPLFQDFIKGYNC
TVLVYGMTSTGKTYTMTGDEKLYNGELSDAAGIIPRVLLKLFDTLELQQNDYVVKCSF
IELYNEELKDLLDSNSNGSSNTGFDGQFMKKLRIFASSTANNTTSNSASSSRSNSRNS
SPRSLNDLTPKAALLRKRLRTKSLPNTIKQQYQQQQAVNSRNNSSSNSGSTTNNASSN
TNTNNGQRSSMAPNDQTNGIYIQNLQEFHITNAMEGLNLLQKGLKHRQVASTKMNDFS
SRSHTIFTITLYKKHQDELFRISKMNLVDLAGSENINRSGALNQRAKEAGSINQSLLT
LGRVINALVDKSGHIPFRESKLTRLLQDSLGGNTKTALIATISPAKVTSEETCSTLEY
ASKAKNIKNKPQLGSFIMKDILVKNITMELAKIKSDLLSTKSKEGIYMSQDHYKNLNS
DLESYKNEVQECKREIESLTSKNALLVKDKLKSKETIQSQNCQIESLKTTIDHLRAQL
DKQHKTEIEISDFNNKLQKLTEVMQMALHDYKKRELDLNQKFEMHITKEIKKLKSTLF
LQLNTMQQESILQETNIQPNLDMIKNEVLTLMRTMQEKAELMYKDCVKKILNESPKFF
NVVIEKIDIIRVDFQKFYKNIAENLSDISEENNNMKQYLKNHFFKNNHQELLNRHVDS
TYENIEKRTNEFVENFKKVLNDHLDENKKLIMHNLTTATSAVIDQEMDLFEPKRVKWE
NSFDLINDCDSMNNEFYNSMAATLSQIKSTVDTSSNSMNESISVMKGQVEESENAISL
LKNNTKFNDQFEQLINKHNMLKDNIKNSITSTHSHITNVDDIYNTIENIMKNYGNKEN
ATKDEMIENILKEIPNLSKKMPLRLSNINSNSVQSVISPKKHAIEDENKSSENVDNEG
SRKMLKIE

FIGURE 4

```
   1 aacggaagaa atcttgctgc ttagcttctt cgacaactgg agcaccttcg attactacaa
  61 ccgtgtcata tccaacaggt ttagttacat taagcttaac ttccagttca gaaacatcga
 121 tttcctcgtc ctttacgacg atttgatcct taatttcctc aattaggatt tccgacattt
 181 ctggtgtagt gccgttgtct ctagtcaagt ttcttcaccc agtgactggg gggacatcga
 241 agagtaactt tagagaaatt taaaaaaaat tgaaagtaat gaaagtaga atttaaaaaa
 301 catggtatca tttaaaataa actaataaag ttgattctgt tttatatttc ttctttttta
 361 gattttaact cattctaccg attttgacta ttatcattac tgacaacagt ttatctgcca
 421 agttcgttca ttttgtattg attttagta ttagcacaat tgttggattt ttcataaaag
 481 ttctttttc tcctttttat actgttgatt tgtactgcaa aacattggaa tgagacattc
 541 caagtgttac cgtgtctgag tcctcgttct tgtttacaac aattcaacaa catactcagg
 601 agcgaacaat tgtccaattt attcattctt tttacccta aaaacagacg tttacgatct
 661 tttcctattt taaatttacc ccttttttt atattgtggt ttattgaact ttacaacaga
 721 attgcaattt aaattaacaa ccttgtcgct ttctttgtaa caatccttac tcataaaacc
 781 gaatggcccc tagagttgca cctggtggct cacaacaatt tctaggaaag caggggttga
 841 aagctaaaaa cccggtttct actccaaatt cacatttccg tctgcagca atcctaggaa
 901 acgacgtgag cctcctacta ttgacactgg gtacccagat cgctccgaca ctaattctcc
 961 gacagatcat gcacttcatg atgagaacga aaccaatatt aacgtagtcg tccgtgttcg
1021 tggtcgtaca gaccaagaag tacgcgacaa tagtagcctt gctgtatcga cttcgggcgc
1081 tatgggtgct gaattggcca tccagtcgga tcttcatcc atgttggtca cgaagacgta
1141 tgcctttgat aaagtctttg gtcctgaagc tgaccagtta atgctattcg aaaattcggt
1201 agcgcccatg ctggagcaag tattgaacgg ctataattgt actatatttg cgtacggaca
1261 aactggaacc ggtaaaacat atactatgtc tggtgatctt agcgattccg atggaattt
1321 gtctgaagga gcaggcctta ttcctcgtgc ccttatcaa ttatttcct ccttggacaa
1381 cagtaatcaa gaatatgctg tcaaatgctc ctattatgaa ctttacaacg aggaaattcg
1441 cgatcttttg gtttccgaag aattgcgaaa gccagctcgt gtttttgaag atacttcgcg
1501 gagagggaac gttgttatta ctggtattga agaaagttat ataaaaatg ctggcgatgg
1561 gttgcgattg ttacgtgaag gctctcaccg gcgtcaagtt gctgctacaa agtgtaacga
1621 tctttcatct cgtagtcatt caatcttcac gataactctg catagaaagg tatcttcggg
1681 aatgacagat gaaactaatt cacttaccat aaataataac tctgatgact tgctgcgcgc
1741 cagcaaactt catatggttg atttggctgg aagcgagaac attggacgtt ctggagctga
1801 aaacaaacgt gctcgagaaa ctgaatgat caatcaatca ctattaacat taggccgagt
1861 aattaatgca ttagtggaaa aggcccacca tattccatac cgtgagtcca agcttacacg
1921 cctattgcag gattctttgg ggggaaagac taaaacctct atgatcgtta ccgtatcttc
1981 tactaatact aatttggaag aaacaatttc tactttggag tatgctgctc gtgctaaaag
2041 tatacgcaat aagcctcaaa ataatcagct tgtcttcga aaagtcctta taaaagactt
2101 agtgttagat atcgaacgat tgaaaaatga ccttaatgcc acccgtaaaa agaacggagt
2161 ttatcttgct gaaagcacgt ataaggagct tatggatcgt gttcaaaaca aagatttgtt
2221 atgccaggaa caggctcgca aacttgaagt gctggactta aacgttaaaa gttcgaggga
2281 acaactgcag tatgtttcta aatctaatca agaacataaa aaggaagttg aagctctgca
2341 actgcaactg gttaattcat ctacagagtt agaaagtgta aagtctgaga acgaaaagct
2401 gaaaaatgaa ctagttttag aaatcgaaaa acgaaaaaa tacgaaacca atgaagctaa
2461 aattacaact gttgcaacag accttccca atattccga gaatcaaaag aatacattgc
2521 tagcttatat gagaagcttg atcgcactga acgaaataat aaagaaaatg aaaacaattt
2581 ttggaatctt aagttcaatt tgttaacgat gttgagatct tttcatggaa gttttactga
2641 tgaaacaaat ggctatttta ctttgttgaa tgattttaat gcttcaatgg aagaattatt
2701 gaacacccac agtaatcaac tgctgatttc tatgaccaaa attactgagc attttcagag
2761 tttagatgag gcgttgcaaa gtgctcgttc ttcttgtgca gtacctaatt ctagcttaga
2821 cctaattgtt tctgaattaa aggattccaa aaacagcctt cttgatgcgt tggagcacag
2881 tctgcaggat attagcatgt cttcccagaa gttgggaaat ggaatttctt cggaattgat
2941 agaattgcag aaagacatga agaatcata ccgacaactt gttcaggaat taagatcact
3001 atataattta cagcatactc atgaagaatc acagaaggag ctaatgtatg gtgtgcgtaa
3061 cgatattgat gctctggtta aaacttgcac aacatctttg aacgatgcag atataatatt
```

FIGURE 5A

```
3121 aagtgattac atatctgatc aaaaatccaa atttgaatcc aagcaacaag atttgattgc
3181 taatattggt aaaattgttt caaatttttt acaggaacag aacgaatctt tgtataccaa
3241 agcggatatc ttacattcac atctcaatga tacaaactcg aatataagga aagcaaacga
3301 aattatgaat aaccgttcag aagagttttt acggaatgcg gcttcacaag cagaaatcgt
3361 gggtgccaat aaagaaagga ttcaaaagac agttgaaaat ggatctcaac tgcttgacag
3421 taaaagcaag gccattcata gcaattccag atcaatgtat gaccattgct tggctttagc
3481 ggagtctcaa aaacaaggtg ttaatcttga agttcaaacg ctggatcgtt tgttgcagaa
3541 agtaaaagag cattcagaag ataataccaa ggagaagcat caacaattac ttgatttatt
3601 ggaatccctt gttggcaaca atgacaatct tatcgattcc atcaagacac cgcacactga
3661 attacagaaa attacagatc atgttttaaa gggaacgaca tcacttgcta atcatactaa
3721 tgaattactt ggtttaggag atgaatctct atgtaacctt gaaactacta tagaagacac
3781 gtctttggtg aagctggaaa caactggcga tacaccttcc aaacgagaac ttcctgccac
3841 tccatcttgg acacgagatt cgtctttaat taaggaaact acgaatttaa atttagattc
3901 ggataagaaa ttcgttaggg aaacctacac atcgtctaat caaactaatg agccggacgt
3961 atatgataaa ccatctaatt catcaagaac tagtcttttg cggagtagca gaagtgccta
4021 ttccaaaatg aaacgataat gacacgattt tattaattta tacttaatgg acgaaaatac
4081 aatagaaatg tattacatct tggggctttg gctggttaaa acggaaagtt tggttatgtg
4141 tgtacatact gcgttttaaa taatagtttt aggagttgta tacatataaa gattaattta
4201 gatagaagtt taatgatata cag
```

FIGURE 5B

```
MAPRVAPGGSQQFLGKQGLKAKNPVSTPNSHFRLRAILGNDVSL
LLLTLDHALHDENETNINVVVRVRGRTDQEVRDNSSLAVSTSGAMGAELAIQSDPSSM
LVTKTYAFDKVFGPEADQLMLFENSVAPMLEQVLNGYNCTIFAYGQTGTGKTYTMSGD
LSDSDGILSEGAGLIPRALYQLFSSLDNSNQEYAVKCSYYELYNEEIRDLLVSEELRK
PARVFEDTSRRGNVVITGIEESYIKNAGDGLRLLREGSHRRQVAATKCNDLSSRSHSI
FTITLHRKVSSGMTDETNSLTINNNSDDLLRASKLHMVDLAGSENIGRSGAENKRARE
TGMINQSLLTLGRVINALVEKAHHIPYRESKLTRLLQDSLGGKTKTSMIVTVSSTNTN
LEETISTLEYAARAKSIRNKPQNNQLVFRKVLIKDLVLDIERLKNDLNATRKKNGVYL
AESTYKELMDRVQNKDLLCQEQARKLEVLDLNVKSSREQLQYVSKSNQEHKKEVEALQ
LQLVNSSTELESVKSENEKLKNELVLEIEKRKKYETNEAKITTVATDLSQYYRESKEY
IASLYEKLDRTERNNKENENNFWNLKFNLLTMLRSFHGSFTDETNGYFTLLNDFNASM
EELLNTHSNQLLISMTKITEHFQSLDEALQSARSSCAVPNSSLDLIVSELKDSKNSLL
DALEHSLQDISMSSQKLGNGISSELIELQKDMKESYRQLVQELRSLYNLQHTHEESQK
ELMYGVRNDIDALVKTCTTSLNDADIILSDYISDQKSKFESKQQDLIANIGKIVSNFL
QEQNESLYTKADILHSHLNDTNSNIRKANEIMNNRSEEFLRNAASQAEIVGANKERIQ
KTVENGSQLLDSKSKAIHSNSRSMYDHCLALAESQKQGVNLEVQTLDRLLQKVKEHSE
DNTKEKHQQLLDLLESLVGNNDNLIDSIKTPHTELQKITDHVLKGTTSLANHTNELLG
LGDESLCNLETTIEDTSLVKLETTGDTPSKRELPATPSWTRDSSLIKETTNLNLDSDK
KFVRETYTSSNQTNEPDVYDKPSNSSRTSLLRSSRSAYSKMKR
```

FIGURE 6

```
   1 tttttttttc agggtgccgt gttgcggtca cactatttgc gcattatttt aaaattgaac
  61 ggacaactga agacgctgct tctctctgtt ctcattggaa atagtgcgaa aattggtttt
 121 ccacgccagc cttctgtaaa tagtagttac agttatcagc attcggctcg gtggaaggtg
 181 aagcacaagg atttccagga atcaaacaca cacacacacg cataccgata cacgcgacag
 241 gcgtcatttt ttggactgta cgcgctaaaa ccacaattaa ttgtttcaat tgatcaatat
 301 ggacatatct ggtgggaata cgtcgcgcca gccccaaaag aagtccaacc aaaacatcca
 361 ggtgtatgtg cgcgtcagac cccttaattc tcgggaacgt tgcatccgct cggccgaagt
 421 cgtggatgtg gtcggaccac gggaagtggt cacccgccac acgctggact ccaagctcac
 481 caagaagttc acctttgacc gcagttttgg ccccgagtcc aagcagtgcg atgtctactc
 541 cgtcgtggtg tctccgctga tcgaggaggt cctcaatggc tataactgca cggtgtttgc
 601 ttatggccag acgggcacag ggaagaccca ccatggtg ggcaacgaga ctgccgaact
 661 gaaatcctcc tgggaagatg actctgacat tggcatcata ccgcgcgctc tgagtcacct
 721 tttcgatgag ctgcgcatga tggaggtgga gtacactatg cgcatttcct acttggaact
 781 gtacaatgag gagctgtgcg atctactgtc caccgatgac accaccaaga tacgcatttt
 841 cgatgacagc accaagaagg gatcggtgat tatccagggc ctggaggaga taccagtgca
 901 cagcaaggat gatgtgtaca agctgctgga aagggaaag gagcgtcgca aaacagccac
 961 tacgctgatg aatgcacagt cctcacgctc ccacactgta ttttctatag ttgtgcacat
1021 cagggagaat ggcatcgaag gagaggacat gctgaaaatc ggtaaactga atctggtgga
1081 tctggcgggc agtgaaaatg tttccaaggc tgggaatgaa aagggaatac gtgtgcggga
1141 aacagtaaac atcaatcaga gcctcttgac tctcggtaga gtaattaccg ctttggtcga
1201 tcgcgctcct cacgttccat atcgtgaatc aaagctgact agactgctgc aagaatctct
1261 gggtggcagg accaagacct ccatcatagc caccatatcg ccgggccaca aggacatcga
1321 ggagaccctg agcactttag agtacgctca tcgcgccaag aacattcaaa acaagcccga
1381 agtcaatcag aagctgacca aaaagactgt gctcaaggaa tacaccgaag aaatcgacaa
1441 gcttaaaaga gatcttatgg cggccaggga caagaatggc atctatttgg ccgaggaaac
1501 ctacggggag ataactttga agttagaatc ccagaaccgc gagcttaacg agaaaatgct
1561 gctgctcaag gctttgaagg acgaactcca gaacaaggag aagatcttca gtgaggtgag
1621 catgagtctt gtggagaaaa cgcaggagct gaaaaagacc gaggagaacc tactgaacac
1681 gaagggtact ttgctcctga ccaagaaagt gctgaccaag accaagcgac gatacaagga
1741 aaaaaggag ttggtggcct cgcatatgaa aacggagcag gttttgacca cacaggctca
1801 ggagatccta gccgctgctg atctggccac tgatgatact catcagctgc acggaaccat
1861 cgaaagaagg cgtgagttgg atgagaagat tcgccgatct tgcgatcagt tcaaagatcg
1921 tatgcaggat aatttggaaa tgatcggtgg cagcctgaac ttgtatcagg atcagcaggc
1981 agccctcaag gagcagctaa gccaggaaat ggtaaactcg agctatgtga gccaacgcct
2041 tgcactaaat tccagcaaaa gcatcgaaat gcttaaggag atgtgtgccc aatcgctaca
2101 ggatcagacc aacctccata ataagttaat aggagaagtc atgaagatca gcgatcagca
2161 ctctcaggca tttgtcgcca agctgatgga gcagatgcag cagcaacagc ttttgatgag
2221 caaagaaatt cagactaacc tgcaggtgat cgaggaaaac aaccagcggc acaaagccat
2281 gctggactct atgcaggaaa agttcgccac cataattgac agcagcttac agtctgtgga
2341 agaacatgcg aagcaaatgc acaagaagtt ggagcagctc ggggcaatga gtttgccaga
2401 tgcggaggaa ctgcagaatc ttcaagagga gttggcgaat gaacgagctc tggcgcagca
2461 ggaggatgct ctccttgagt ccatgatgat gcagatggaa cagatcaaga acttgcggtc
2521 caaaaatagc atcagcatgt ccgtacatct taataagatg gaggagagtc gactgacgag
2581 aaatcatcgc atcgatgata ttaagtctgg tatccaagac taccaaaagt gggcataga
2641 agcttcccaa tccgcacaag cggagctcac cagccaaatg gaggcgggaa tgctttgtct
2701 ggaccaaggc gttgccaact gttcgatgct tcaggtgcac atgaagaatc tcaaccagaa
2761 atacgaaaag gaaacaaatg agaatgttgg ttccgttcga gtgcaccaca atcaggtgga
2821 aattatttgc caagagagca agcagcagct tgaggcggtg caggagaaaa ccgaagttaa
2881 cttggaacag atggtggatg caaggcagca gcttatcacc gaggacagac agcgattcat
2941 aggccatgcc actgtagcca ctgatcttgt ccaagagtcg aaccggcagt tctcggagca
3001 tgctgaacac caacggcagc agctgcaaat ttgcgagcaa gagcttgtac gcttccaaca
3061 gtcggagttg aaaacgtacg ccccaactgg gaccacgccc tccaaaaggg atttcgttta
```

FIGURE 7A

```
3121 tccgcgcacc ctcgtggcca cgtcgccaca tcaggaaatt gtgaggcgct atcgccaaga
3181 gcaggactgg tcagatctgg acaccacggc cactatagat gagtgcagcg agggtgagca
3241 tgacgactcc atgcattccg tccaggagct gtccgaaact gaaaccataa tgaactccac
3301 gcccattgag cccgtggatg gtgtcaccgt gaagcgtggg tgcggcacca cccgcaattc
3361 caattcgaac gccctaaagc cacccgtagc tactggtgga aaacgcagca gtcgttgtc
3421 acgttccctg acacccagta aaacgtcacc tcgaggttct cccgccttcg tcaggcacaa
3481 caaagaaaac gtagcctgat tgcattcgat gacagtagta gtctccccct cccagtaacc
3541 cgtttatgtt agtggatttc ggatcgctgt gtttgtttgg ctcttctgga tattcatttt
3601 atctgtatat caatctttgg aatttcgtac atttattatt taaataaact cagtatgcta
3661 tgtaaagtta aaaaaaaaaa aaaaaaaaaa aaaaaaaaaa aaaaaaaa
```

FIGURE 7B

MDISGGNTSRQPQKKSNQNIQVYVRVRPLNSRERCIRSAEVVDV
VGPREVVTRHTLDSKLTKKFTFDRSFGPESKQCDVYSVVVSPLIEEVLNGYNCTVFAY
GQTGTGKTHTMVGNETAELKSSWEDDSDIGIIPRALSHLFDELRMMEVEYTMRISYLE
LYNEELCDLLSTDDTTKIRIFDDSTKKGSVIIQGLEEIPVHSKDDVYKLLEKGKERRK
TATTLMNAQSSRSHTVFSIVVHIRENGIEGEDMLKIGKLNLVDLAGSENVSKAGNEKG
IRVRETVNINQSLLTLGRVITALVDRAPHVPYRESKLTRLLQESLGGRTKTSIIATIS
PGHKDIEETLSTLEYAHRAKNIQNKPEVNQKLTKKTVLKEYTEEIDKLKRDLMAARDK
NGIYLAEETYGEITLKLESQNRELNEKMLLLKALKDELQNKEKIFSEVSMSLVEKTQE
LKKTEENLLNTKGTLLLTKKVLTKTKRRYKEKKELVASHMKTEQVLTTQAQEILAAAD
LATDDTHQLHGTIERRRELDEKIRRSCDQFKDRMQDNLEMIGGSLNLYQDQQAALKEQ
LSQEMVNSSYVSQRLALNSSKSIEMLKEMCAQSLQDQTNLHNKLIGEVMKISDQHSQA
FVAKLMEQMQQQQLLMSKEIQTNLQVIEENNQRHKAMLDSMQEKFATIIDSSLQSVEE
HAKQMHKKLEQLGAMSLPDAEELQNLQEELANERALAQQEDALLESMMMQMEQIKNLR
SKNSISMSVHLNKMEESRLTRNHRIDDIKSGIQDYQKLGIEASQSAQAELTSQMEAGM
LCLDQGVANCSMLQVHMKNLNQKYEKETNENVGSVRVHHNQVEIICQESKQQLEAVQE
KTEVNLEQMVDARQQLITEDRQRFIGHATVATDLVQESNRQFSEHAEHQRQQLQICEQ
ELVRFQQSELKTYAPTGTTPSKRDFVYPRTLVATSPHQEIVRRYRQEQDWSDLDTTAT
IDECSEGEHDDSMHSVQELSETETIMNSTPIEPVDGVTVKRGCGTTRNSNSNALKPPV
ATGGKRSSSLSRSLTPSKTSPRGSPAFVRHNKENVA

FIGURE 8

```
   1 gaattccgtg cgaggaggcg ctgtagttcc ggagggtctt taacgctgtg ctgtaggagc
  61 ggtgatctca gcgcacgggt tatacatcca ctgtctgccc ggggagggaa atcgtgactg
 121 ccgactggag gtcactatgt cttcccagaa ttctttcatg tctagcaaga aggacgacaa
 181 aggcaaaaac atccaggttg tggtcagatg ccggcccttc aatcagttgg aacgcaaggc
 241 gagctctcac tctgtgttgg aatgcgagtc tcagaggaaa gaagtctgtg ttcgaaccgg
 301 agaagtaaat gacaaactgg ggaagaaaac ctatacgttt gacatggtgt ttggcccggc
 361 agccaagcag atcgatgtgt acagaagtgt tgtgtgcccc atcttggatg aagttattat
 421 gggctataac tgtacaatct ttgcgtatgg gcaaactggc acaggaaaga cttttactat
 481 ggaggggaa agatcatcag atgaagagtt tacctgggag caggacccac tggcaggaat
 541 tattcctcga acgctgcatc agatatttga gaagctctct gagatcggca cagagttttc
 601 ggtgaaagtc tcactcctgg aaatctacaa tgaagaactc tttgatctct taagcccatc
 661 tcccgatgtc ggggaaaggc tacaaatgtt tgacgatcct cgcaacaaaa gaggagtcat
 721 tatcaaaggg ctggaggaga tatctgtgca taacaaagat gaggtgtacc aaatattgga
 781 gagaggcgca gctaagcgaa aaactgcttc tactctgatg aatgcatact ccagccgatc
 841 ccattccgtg ttctcagtca ccattcacat gaaagaaact acaattgatg gagaagagct
 901 tgtgaagatt ggaaagctaa acttggtgga tctggcggga agtgaaaata ttggccgttc
 961 tggggccgtg gacaaagag cgcgggaggc tggaaatatc aaccagtccc tgctgacctt
1021 gggcagggta atcaccgctc tggtggagag agctcctcat attccataca gagaatccaa
1081 gctcacaagg atcctgcaag attctcttgg agggaggaca aaaacatcta tcatagccac
1141 tgtgtctcct gcctccatca atctggagga aactatgagc actttggact atgccagcag
1201 agcaaagaat ataatgaata agcctgaagt taaccagaaa cttacaaaga aggcactcat
1261 caaggagtac acagaagaga ttgagcgact caagagggaa cttgctacag ccagagagaa
1321 gaacggagtc tatttatcca acgagaacta tgagcaatta cagggaaaag ttctgtctca
1381 agaggagatg attacggagt actctgagaa aatcgctgcc atggaggagg agatcaaaag
1441 aattggtgag cttttttgcgg acaataaaaa ggagctggag gagtgcacga ctatccttca
1501 gtgtaaggag aaggagctgg aggcaacaca gaataacctg caagaatcaa aggaacagtt
1561 ggctcaggaa gcatttgtgg tgtccgccat ggagaccaca gaaaagaagc tacatggcac
1621 tgcaaacaag ttattgagca cagtgagaga gacgacaaga gatgtgtctg gtctccatga
1681 gaaactggac agaaaaaggg ccgtggaaca acacaactct caggttcatg agaactttgc
1741 cgaacaaata aatagacgct tcagtgtgat tcagcaaact gtggatgagt acagcgtgaa
1801 gcagcaaggg atgctggatt tctatacaaa ctccatcgac gacctacttg gcgccagttc
1861 ctctgctctg agtgcaactg ccactgccgt tgccaagtcc tttgcctccg tgcaggaaac
1921 cgtatcaaag caagtgtcgc acagtgtgga ggagatactg aagcaggaaa cactgtcttc
1981 ccaagctaaa gatgatctgc agaagcttat gactgcacac cgcacaggac tggagcaagc
2041 acttaggacg gatttgcttc cagttgtgac tgccgttttg gacctaaatt ctcatttgag
2101 tcattgcttg cagagcttcc taggtgtggc cgacaagatt gattctcata agaagatat
2161 gaattcgttc ttcaccgaac attctaggtc gttgcacaaa cttcgcctgg attcgagttc
2221 tgccttgtcc agtattcagt cagaatatga aagcttaaaa gaggagattg cgacggctca
2281 gtccacgcat tcagagggg tgaataatct catcagttca ctgcagaacc aactgaactt
2341 gcttgccatg gagactcggc aacagttttc tggatttctg tccaaaggag ggaagctgca
2401 ggagtctgtg gggtgtctgc aacaagatct ggacttggtt tcttcagatg ccatagaatg
2461 catctcctcc catcacagca aattcactga gcagtctcag gcggtaacgg tggagatcag
2521 acagctggca ggctctaata tgagcaccct tggaggagtcc agcaaacagt gtgagaagct
2581 caccaacagt atcaatacca tctgtcagga aagccagcag tggtgtgaaa gtgccggcca
2641 gaagatggac tctctcttag aggagcaagt gtgttacctg cattctagca aaaagcaaat
2701 ccagacctta cacaaggatg tagaagatgg ctgtggatca tcagtggtag aaataacgga
2761 ccgcgtgaat gtgcagtgcc aggctcagga gaaggcacta accagcttgg tgaacaagt
2821 caaagatgac aaagagatgc ttggagaaca gcgattggaa ctcaacgaac aagtacagag
2881 cggcctgaac aaagtacatg tatacctcaa ggaggagctc cggaatgatg tcccaacagg
2941 tacaacgccc cagagaaggg attacgtgta cccatcattg ctcataaaaa caaaacccag
3001 ggatgtgttg ctggagcagt ttaggcaaca gcagcaagaa tatctgaat ctatttgcag
3061 cgtgatctct gaagctgtgg aacctcctgt cgagcaggat tctctagaag atgagccacc
3121 agttgcagtt aatgacagtg tcatcagtga gaatcctgc atagatctca gtatgacttg
3181 tcaggagaaa ggaggggttc cattcttcca gcaaagaaa gcacttcgga aggaaaaga
3241 aaacagggga aatgcaacac ttttggagag atctaaaatc atggacgagg tggaacaatc
3301 ccttccgaaa tctaaacttc cactgcgaat gcagaactga agcacttgct cagcctctct
3361 ttttaaccct atgagtgaat gtacaacttt ctttctgtcc tgaacttta tacatttttt
```

FIGURE 9

```
MSSQNSFMSSKKDDKGKNIQVVVRCRPFNQLERKASSHSVLECE
SQRKEVCVRTGEVNDKLGKKTYTFDMVFGPAAKQIDVYRSVVCPILDEVIMGYNCTIF
AYGQTGTGKTFTMEGERSSDEEFTWEQDPLAGIIPRTLHQIFEKLSEIGTEFSVKVSL
LEIYNEELFDLLSPSPDVGERLQMFDDPRNKRGVIIKGLEEISVHNKDEVYQILERGA
AKRKTASTLMNAYSSRSHSVFSVTIHMKETTIDGEELVKIGKLNLVDLAGSENIGRSG
AVDKRAREAGNINQSLLTLGRVITALVERAPHIPYRESKLTRILQDSLGGRTKTSIIA
TVSPASINLEETMSTLDYASRAKNIMNKPEVNQKLTKKALIKEYTEEIERLKRELATA
REKNGVYLSNENYEQLQGKVLSQEEMITEYSEKIAAMEEEIKRIGELFADNKKELEEC
TTILQCKEKELEATQNNLQESKEQLAQEAFVVSAMETTEKKLHGTANKLLSTVRETTR
DVSGLHEKLDRKRAVEQHNSQVHENFAEQINRRFSVIQQTVDEYSVKQQGMLDFYTNS
IDDLLGASSSALSATATAVAKSFASVQETVSKQVSHSVEEILKQETLSSQAKDDLQKL
MTAHRTGLEQALRTDLLPVVTAVLDLNSHLSHCLQSFLGVADKIDSHKEDMNSFFTEH
SRSLHKLRLDSSSALSSIQSEYESLKEEIATAQSTHSEGVNNLISSLQNQLNLLAMET
RQQFSGFLSKGGKLQESVGCLQQDLDLVSSDAIECISSHHSKFTEQSQAVTVEIRQLA
GSNMSTLEESSKQCEKLTNSINTICQESQQWCESAGQKMDSLLEEQVCYLHSSKKQIQ
TLHKDVEDGCGSSVVEITDRVNVQCQAQEKALTSLVEQVKDDKEMLGEQRLELNEQVQ
SGLNKVHVYLKEELRNDVPTGTTPQRRDYVYPSLLIKTKPRDVLLEQFRQQQQEYLES
ICSVISEAVEPPVEQDSLEDEPPVAVNDSVISEKSCIDLSMTCQEKGGVPFFQQKKAL
RKEKENRGNATLLERSKIMDEVEQSLPKSKLPLRMQN
```

FIGURE 10

Figure 14
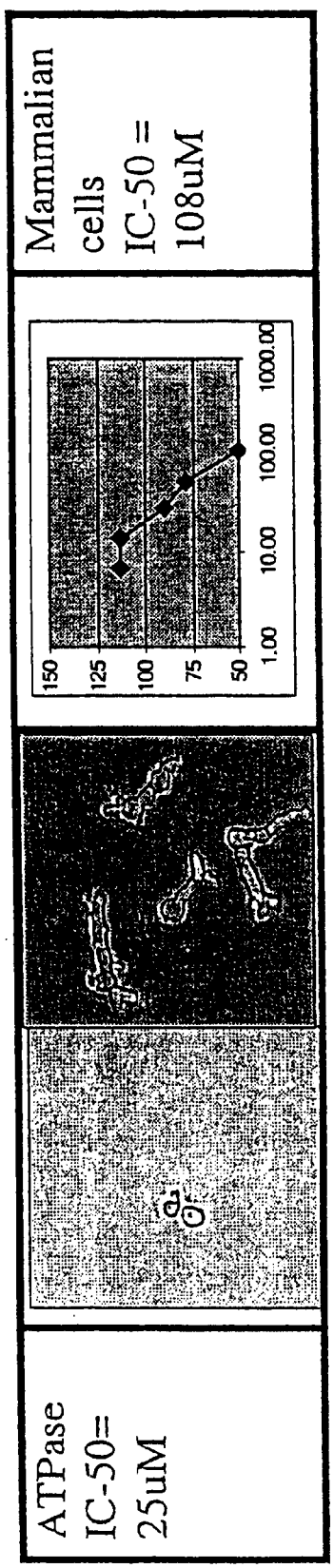
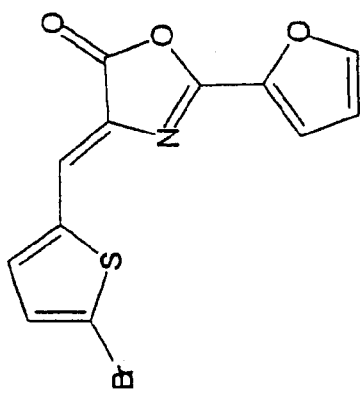
ATPase IC-50= 25uM
*S. cerevisiae*   *A. nidulans*
Mammalian cells IC-50 = 108uM

ANTIFUNGAL ASSAY

This is a Continuation application of prior application No. 09/723,820 filed on Nov. 28, 2000, now U.S. Pat. No. 6,468,760, which is a continuation of application No. 09/541,782 U.S. Pat. No, 6.284.480 issued Sep. 4, 2002 filed Apr. 3, 2000 the disclosure of which is incorporated herein by reference.

FIELD OF THE INVENTION

The invention relates to methods for the identification of compounds that modulate the activity of bimC and use of such methods for the identification of therapeutic agents and agricultural compounds.

BACKGROUND OF THE INVENTION

There is a compelling need to prevent and treat opportunistic fungal infections that result in a variety of manifestations, many of which are fatal if untreated. Indeed, the 1980s witnessed an epidemic rise in Candida infections. A steep rise in the incidence of Aspergillus infections has occurred during the 1990's. Similar rises in zygomycosis, cryptococcosis, histoplasmosis and fusaria infection have also been noted. The reasons for the rise in fungal infections are several, but a key factor is the growing population of immuno-compromised individuals. This group includes patients with HIV disease (ADS), older patients, patients who have undergone invasive surgery, transplant patients and burn victims.

Accordingly, the need for novel antifungal drugs is clear. At present there are two accepted therapies, namely, amphotericin B and the azole family of compounds. Both are effective for certain fungal infections but each have drawbacks—amphotericin B is nephrotoxic and there are increasing numbers of azole resistant strains. These drugs act by either directly or indirectly disrupting the fungal cell wall (or its underlying membrane), which has been the target of choice for antifungal agents.

As the population of immunosuppressed individuals increases, so do the numbers and types of fungal infections noted in these patients. Although candidiasis remains the most common fungal infection in immunosuppressed patients, aspergillosis, zygomycosis, and other filamentous fungal infections are a major problem for an increasing number of patients. The endemic mycoses, especially histoplasmosis and coccidioidomycosis, also constitute a risk for patients. Those at particular risk for such infections are those with AIDS, those having undergone bone marrow or organ transplants, those receiving chemotherapy and others who have had debilitating illness, severe injury, prolonged hospitalization, or longterm treatment with antibacterial drugs.

According to the CDC's National Nosocomial Surveillance System, the rate of hospital-related fungal infections nearly doubled between 1980 and 1990. In 1997, an estimated 240,000 individuals showed clinical symptoms of endemic mycoses. With the current approaches to treatment (primarily amphotericin B and the azoles) the mortality rate in patients with systemic fungal infections ranges from 30–100%, depending on the infection, The severity of the fungal infections increases as the immune system becomes more dysfunctional. Fungi are among the most ubiquitous pathogens seen in patients with AIDS; virtually all major fungal pathogens cause disease in HIV-positive patients. The majority of untreated HIV-positive patients experience at least one episode of fungal infection and many fungal infections are AIDS-defining illnesses in AIDS patients.

Many emerging fungal pathogens are resistant to the currently available antifungal agents and, thus, pose a special risk for immunocompromised patients. Furthermore, as existing therapies are limited in the range of fungal pathogens against which they show efficacy, and as identification of the fungal pathogen infecting an individual is slow relative to the urgent need to control the infection, there is a critical need to develop broad-spectrum antifungal therapeutics.

Clinically relevant mycotic diseases include candidiasis, aspergillosis, cryptococcosis, endemic mycoses and infections caused by a host of new, emerging fungal pathogens. The standard of care for the more common mycoses employs amphotericin B and the triazole family of therapeutics. These treatments are far from ideal; substantial side effects are seen with amphotericin B. For the azoles problematic issues include increasingly resistant strains and limited bioavailability. Finally, for some of the endemic mycoses as well as new emerging fungal pathogens, no appropriate therapeutics are available. The best prospect for combating existing and emerging threats is through the development of broad-spectrum antifungals.

Given the increased numbers of patients manifesting mycotic diseases, combined with the lack of effective antifungals and the increase in azole resistant isolates, there is a compelling need for novel antifungals. The present invention provides a novel method to identify such antifungals.

SUMMARY OF THE INVENTION

The present invention provides methods to identify candidate agents that bind to a target protein or act as a modulator of the binding characteristics or biological activity of a target protein. In one embodiment, the method is performed in plurality simultaneously. For example, the method can be performed at the same time on multiple assay mixtures in a multi-well screening plate. Furthermore, in a preferred embodiment, fluorescence or absorbance readouts are utilized to determine activity. Thus, in one aspect, the invention provides a high throughput screening system for detecting modulators of bimC enzyme activity.

Preferably, the target protein either directly or indirectly produces ADP or phosphate. More preferably, the target protein comprises bimC or a fragment thereof.

The method further comprises adding a candidate agent to a mixture comprising the target protein under conditions that normally allow the production of ADP or phosphate. The method further comprises subjecting the mixture to an enzymatic reaction that uses said ADP or phosphate as a substrate under conditions that normally allow the ADP or phosphate to be utilized and determining the level of activity of the enzymatic reaction as a measure of the concentration of ADP or phosphate. The phrase "use ADP or phosphate" means that the ADP or phosphate are directly acted upon by detection reagents. In one case, the ADP, for example, can be hydrolyzed or can be phosphorylated. As another example, the phosphate can be added to another compound. As used herein, in each of these cases, ADP or phosphate is acting as a substrate. A change in the level between the presence and absence of the candidate agent indicates a modulator of the target protein.

Also provided are modulators of the bimC subfamily of kinesins including antifungal agents. The agents and compositions provided herein can be used in variety of applications which include the formulation of sprays, powders, and other compositions in the formulation of antifungal preparations which can be used to prevent the growth of fungi. Also provided herein are methods of preventing and treating fungal infections.

BRIEF DESCRIPTION OF THE DRAWINGS

FIGS. 1A and 2B show the nucleic acid sequence of an embodiment of bimC (SEQ ID NO:1).

FIG. 2 shows the amino acid sequence of an embodiment of bimC (SEQ ID NO:2).

FIGS. 3A and 3B show the nucleic acid sequence of a bimC homolog, cin8 (SEQ ID NO:3).

FIG. 4 shows the amino acid sequence of cin8 (SEQ ID NO:4).

FIGS. 5A and 5B show the nucleic acid sequence of a bimC homolog, cut7 (SEQ ID NO:5).

FIG. 6 shows the amino acid sequence of cut7 (SEQ ID NO:6).

FIGS. 7A and 7B show the nucleic acid sequence of a bimC homolog, KLP61 (SEQ ID NO:7).

FIG. 8 shows the amino acid sequence of KLP61 (SEQ ID NO:8).

FIG. 9 shows the nucleic acid sequence of a bimC homolog, Eg5 (SEQ ID NO:9).

FIG. 10 shows the amino acid sequence of Eg5 (SEQ ID NO:10).

FIG. 14 shows the results of the testing of representative candidate agents against S. cerevisiae, A. nidulans and mammalian cells. In this experiment fungal cells were incubated with 2–50 µM of each compound and assayed for growth over time at 25° C. The phenotypes shown were obtained after 4 days incubation at 25° C. In these graphs the dotted line represents cell count at various dilutions serving as a measure of cellular viability.

DETAILED DESCRIPTION OF THE INVENTION

I. Definitions

Figure 11:
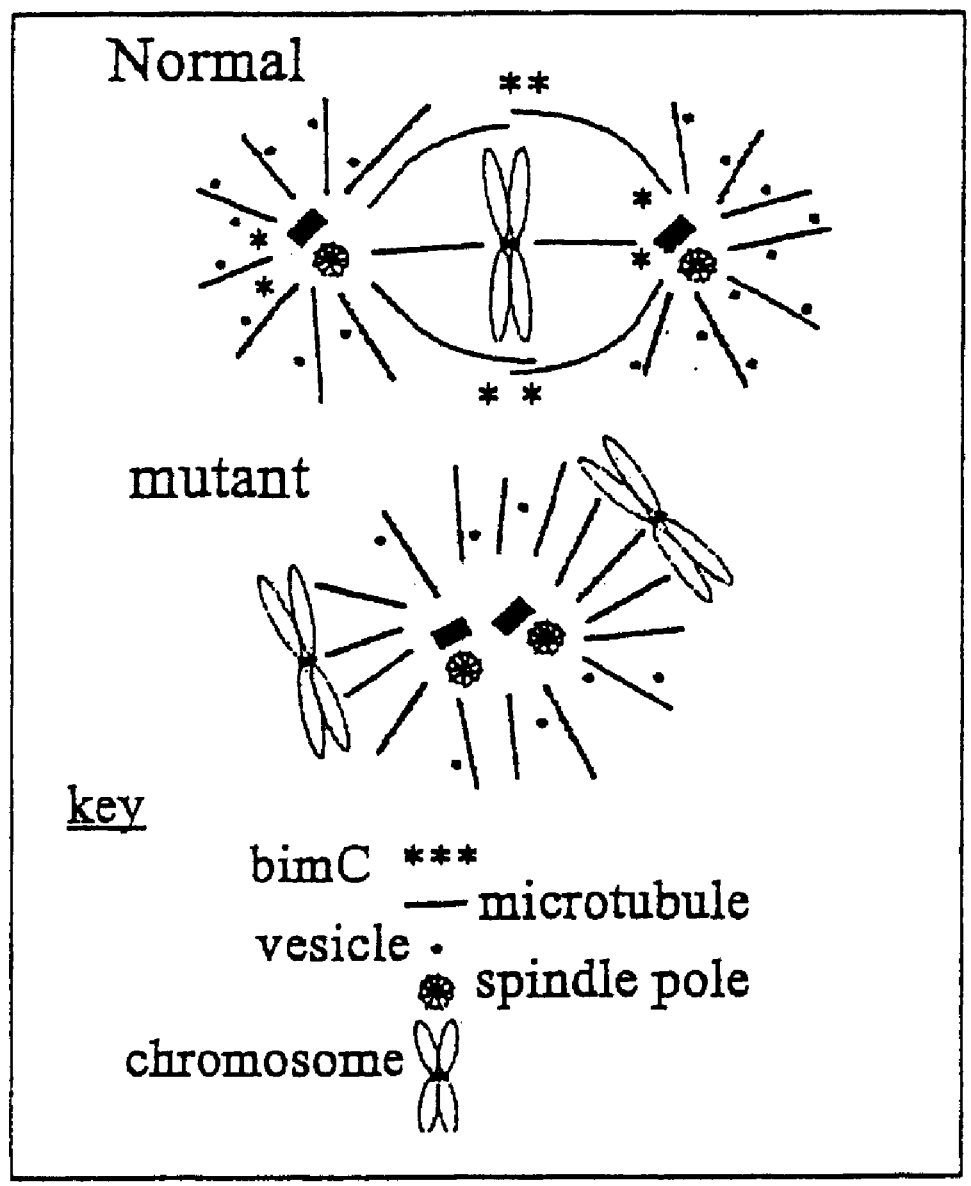
FIG. 11 illustrates the proposed roles for bimC family members during mitosis. The top panel (normal spindle) shows a normal bipolar mitotic spindle at metaphase. The bottom panel (mutant spindle) shows the abnormal morphology of spindles at a comparable mitotic stage in organisms carrying mutations in bimC family motor proteins. BimC family mutants are characterized by the formation of monastral microtubule arrays containing duplicated spindle poles that fail to separate.

An "agricultural compound" as used herein refers to a chemical compound that has utility in agriculture and functions to foster food or fiber crop protection or yield improvement. For example, one such compound may serve as a fungicide to control the spreading of plant diseases.

"Cytoskeletal component" denotes any molecule that is found in association with the cellular cytoskeleton, that plays a role in maintaining or regulating the structural integrity of the cytoskeleton, or that mediates or regulates motile/mechanical events mediated by the cytoskeleton. The term includes cytoskeletal polymers (e.g., actin filaments, microtubules, myosin fragments, intermediate filaments), molecular motors, and cytoskeleton associated regulatory proteins (e.g., tropomyosin, alpha-actinin). It is understood that the definitions which apply to the cytoskeletal system apply to embodiments which are drawn to specific components of the cytoskeletal system.

"Cytoskeletal function" refers to biological roles of the cytoskeleton: to provide structural organization (e.g., microvilli, mitotic spindle) and to mediate motile/mechanical events of the cell (e.g., muscle contraction, mitotic contractile ring, pseudopodal movement, active cell surface deformations, vesicle formation and translocation, mitosis (DNA division), cytokinesis (cell division), intracellular (vesicle) transport, cell polarity and organization, cell motility, muscle contractility.

The terms "isolated", "purified", or "biologically pure" refer to material which is substantially or essentially free from components which normally accompany it as found in its native state.

"Molecular motor" refers to a cytoskeletal molecule that utilizes chemical energy to produce mechanical force, and drives the motile, mechanical, or structural/organizational properties of the cytoskeleton.

By "ATPase" herein is meant an enzyme that hydrolyzes ATP. ATPases include proteins comprising molecular motors such as kinesins, dyneins, and myosins.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

"Candidate agent" (used interchangeably herein with "test composition" and "test compound" and "test agent") refers to a molecule or composition whose effect on the interaction between two or more cytoskeletal components it is desired to assay. The "test composition" can be any molecule or mixture of molecules, optionally in a suitable carrier.

A "therapeutic" as used herein refers to a compound which is believed to be capable of modulating the cytoskeletal system in vivo which can have application in both human and animal disease. Modulation of the cytoskeletal system would be desirable in a number of conditions including, but not limited to: fungal diseases such as aspergillosis, candidiasis, and topical fungal diseases.

II. The Target Protein

A. Overview

The cytoskeleton in mammalian cells is an excellent target for anti-cancer compounds as demonstrated by the effectiveness of taxol and other microtubule poisons. The components of the fungal cytoskeleton, specifically its microtubules and associated proteins, are distinct from their mammalian counterparts. These differences at the primary sequence level and at the structural level may provide the requisite specificity to target the fungal cytoskeleton while leaving the mammalian cytoskeleton unaffected. As an example, the small molecule inhibitor, benomyl, is a potent inhibitor of fungal tubulin, but has no effect on mammalian tubulin. Though benomyl has the specificity required for an effective antifungal, its human toxicity (which is unrelated to its action on microtubules) precludes its use on patients.

B. BimC

*Aspergillus nidulans* bimC is a kinesin related protein (KRP) whose gene product encodes an essential mitotic KRP. BimC is the founding member of the bimC subfamily of mitotic kinesins (Morris NR, Enos AP. (1992) Trends Genet 8:1 32–7). Mutants in bimC are blocked in mitosis and arrest with duplicated but unseparated spindle poles. (Enos AP, Morris NR. (1990) Cell 60:6 1019–27). Following the discovery that bimC encodes a KRP, several bimC family members have been identified in diverse organisms ranging from yeast to humans. See. FIG. 1. As described below (Table 1), bimC is unique among fungal kinesins in being essential for viability in all fungi in which it has been tested. Although bimC homologs have been found in diverse organisms, the fungal members of this kinesin subgroup form a "fungal-specific cluster".

Figure 12:
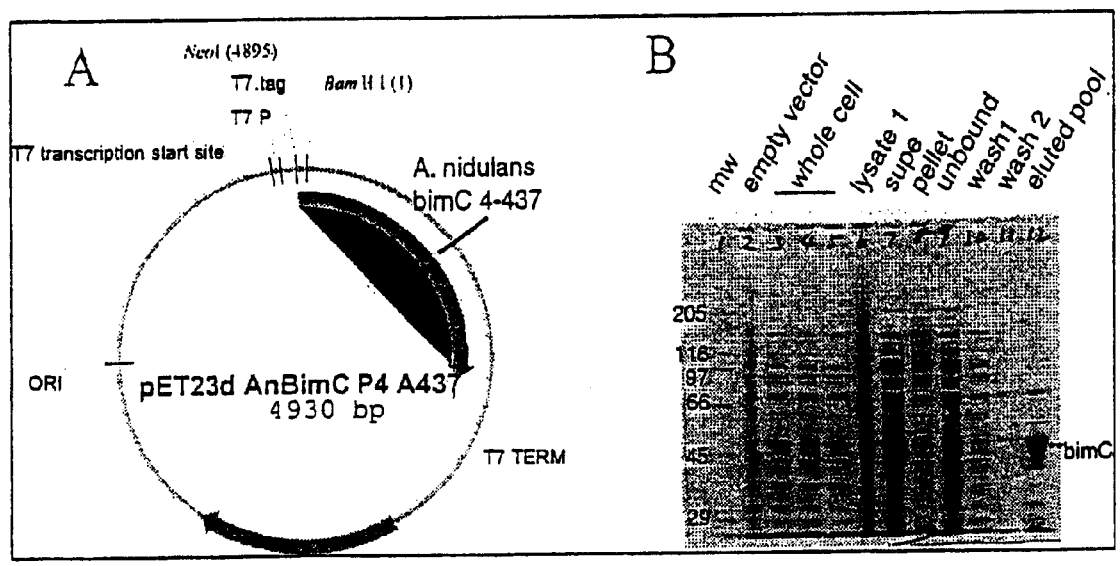
FIG. 12 depicts the cloning and expression of A. nidulans bimC motor domain. In Panel A, an overview of the express is shown. The fragment containing the bimC motor domain is indicated by a filled semi-circle. In B, a Coomassie stained gel of the purification of bimC motor domain is shown.

In a particularly preferred embodiment, a fragment of the bimC protein comprising its hydrolytically active "motor" domain is used. This motor domain has been cloned and expressed in bacteria such that large quantities of biochemically active, substantially pure protein are available (FIG. 12). The expressed protein can be purified by standard chromatographic procedures to yield a purified, biochemically active protein.

TABLE 1

Representative bimC homologs

| Species/protein | kDa | Local-ization | Comments |
|---|---|---|---|
| A. nidulans bimC | 132 | Pole separation | Essential for SPB separation in mitosis, mutants arrest with monopolar spindles |
| D. melanogaster Klp61F | 121/130 | ND | Essential for centrosome separation in mitosis, mutants > monopolar spindle, homotetramer |
| H. sapiens KSP (HsEg5) | 121 | ND | Essential for centrosome separation in mitosis, depletion leads to arrest with monopolar spindle |
| S. cerevisiae Cin8 | 118 | Spindle | Required for separation of spindle poles, formation & maintenance of bipolar spindle |
| S. cerevisiae Kip1 | 126 | Spindle, poles | Redundant with Cin8 |
| S. pombe Cut7 | 121 | Spindle, poles | Required for SPB separation, spindle formation |
| X. laevis Eg5 | 119 | Spindle MTs | Required for spindle formation in vitro |

C. Cut7

In S. pombe, two loci were identified which, when mutated, block spindle formation. Hagan I, Yanagida M. (1990) Nature 11(347):6293 563–6) The predicted product of one of these genes, cut7+, contains an amino-terminal domain similar to the kinesin heavy chain motor domain. See FIGS. 5 and 6. The cut7+gene most closely resembles the *Aspergillus nidulans* spindle motor gene bimC. Kinesin-related cut7 protein associates with mitotic and meiotic spindles (Hagan and Yanagida, 1992) and mutations in cut7+affect spindle integrity. (Hagan I, Yanagida M. (1992) Nature 5 356:6364 74–6). In both wild type *Aspergillus nidulans* and *Schizosaccharomyces pombe* the intranuclear spindle is bipolar, with microtubules that emanate from spindle pole bodies at either pole interdigitating in a central overlap zone. In bimC and cut7 mutants, microtubule interdigitation does not appear to take place; instead, two unconnected half spindles form and chromosome separation fails.

D. CIN8 and KIP1 (*Saccharomyces cerevisiae*)

CIN8 and KIP1 encode polypeptides related to the heavy chain of the microtubule-based force-generating enzyme kinesin, specifically to those within the bimC subfamily (Hoyt, M. A., He, L, Loo, K K, Saunders W S. (1992) J Cell Biol 118:109–120; Roof, D. M., Meluh, P B, Rose MD. (1992) J Cell Biol 118:95–108; and Saunders, W. S. and M. A. Hoyt. (1992) Cell 70:451–458). Cin8p was found to be required for pole separation during mitotic spindle assembly at 37° C. in temperature sensitive mutants, although overproduced Kip1p could suppress the cin8 mutant phenotype. See FIGS. 3 and 4. At lower temperatures, the activity of at least one of these proteins was required for cell viability, indicating that they perform an essential but redundant function. Cin8p was observed to be a component of the mitotic spindle, colocalizing with the microtubules that lie between the poles. Accordingly, Cin8p and Kip1p perform an essential role in the separation of spindle poles during spindle assembly and a major role in spindle elongation.

E. Other Homologs

Outside the fungal realm, bimC homologs have been described in *Drosophila melanogaster* (KLP61F/KRP130) (see FIGS. 7 and 8), *Xenopus laevis* (Eg5), *Homo sapiens* (hsEg5/KSP) (see FIGS. 9 and 10) and other organisms (Table 1). In each case, these homologs are required for the formation and maintenance of a normal, bipolar mitotic spindle. It should be noted, however, that these non-fungal homologs are phytogenetically divergent from their fungal counterparts.

F. The Target Protein

In one aspect, the assays or methods provided include the use of bimC. The context in which the bimC is used will indicate whether the sequence is an amino acid sequence, nucleic acid sequence or other. In preferred embodiments, the bimC is isolated from fungi. In one embodiment, bimC as used herein includes bimC homologs. In a preferred embodiment, the bimC homologs are isolated from fungi or yeast. Preferably, the bimC homologs have a sequence or other structural feature that distinguishes the homologs from mammalian homologs.

III. High Throughput Screening

The present invention provides methods to identify candidate agents that bind to a target protein or act as a modulator of the binding characteristics or biological activity of a target protein. In one embodiment, the method is performed in plurality simultaneously. For example, the method can be performed at the same time on multiple assay mixtures in a multi-well screening plate. Furthermore, in a preferred embodiment, fluorescence or absorbance readouts are utilized to determine activity. Thus, in one aspect, the invention provides a high throughput screening system.

More specifically, the present invention includes methods of screening for compounds effective to modulate molecular motor activity. This assay detects modulators of aspects of kinesin motor function ranging from interaction with microtubules to hydrolysis of ATP. Various molecular motor activities are known in the art and include, but are not limited to, the ability to affect ATP hydrolysis, microtubule binding, gliding, and polymerization/depolymerization (effects on microtubule dynamics), binding to other proteins of the spindle, binding to proteins involved in cell-cycle control, or serving as a substrate to other enzymes, such as kinases or proteases, and specific kinesin cellular activities, such as spindle separation.

In a preferred embodiment, this invention provides an effective method for evaluating the activity of bimC or a fragment thereof in a biochemical assay by monitoring its ability to hydrolyze ATP (ATPase activity). Compounds which modulate the activity of bimC can be found by monitoring the production of either ADP or phosphate by a variety of methods.

In a preferred embodiment, activity is measured by the methods disclosed in Serial No. 09/314,464, filed May 18, 1999, which is incorporated herein by reference in its entirety. These methods are preferably used in multiwell plate formats and are ideally suited for high throughput screening systems to identify lead compounds for medical therapeutic or agricultural uses. More specifically, this assay detects modulators of any aspect of a kinesin motor function ranging from interaction with microtubules to hydrolysis of ATP. The presence of ADP or inorganic phosphate release is used as the readout for protein activity.

The ADP or phosphate level can be monitored using enzyme systems to result in changes in the absorbance or fluorescence of the assay mixture relative to a control mixture to determine if the test compound or mixture of test compounds has an effect on the protein function. This may be done with a single measurement but is preferably done with multiple measurements of the same sample at different times to effect a kinetic profile. In the case of multiple measurements, the absolute rate of the protein activity can be determined, and such measurements have higher specificity particularly in the presence of test compounds that have similar absorbance or fluorescence properties to that of the enzymatic readout. ATP hydrolysis can be measured in a number of spectrophotometric methods.

Methods for ADP determination commonly use the enzyme system pyruvate kinase and lactate dehydrogenase to couple ADP production to the oxidation of NADH. NADH concentration can be monitored by either absorbance (*Proc Natl Acad Sci U S A* 1992 89:4884–4887) or fluorescence (*Biochem J* 1990 266:611–4). Several variations on this method have been reported (U.S. Patent 4,923,796). See also Nature 1956 178:632; *Mol Pharmacol* 1970 Jan;6(1): 31–40. One method for monitoring phosphate production is to use purine nucleoside phosphorylase to couple the phosphate production to the cleavage of a purine analog which results in either a change in absorbance (*Proc Natl Acad Sci U S A* 1992 Jun 1;89(11):4884–7) or fluorescence (*Biochem J* 1990 Mar 1 ;266(2):611–4).

With either method, the rate of ATP hydrolysis by the molecular motor of interest can be measured. Test compounds can be assayed in a highly parallel fashion by using multiwell plates by placing the compounds either individually in wells or testing them in mixtures. Assay components including the molecular motors, protein filaments, coupling enzymes and substrates, and ATP can then be added to the wells and the absorbance or fluorescence of each well of the plate can be measured with a plate reader. A compound which modulates the function of the molecular motor is identified by an increase or decrease in the rate of ATP hydrolysis compared to a control assay in the absence of that compound.

For proteins which use ATP, in addition to methods which measure phosphate or ADP, the remaining ATP can be measured using the luciferin-luciferase system (*Anal Biochem.* 1971 40:1–17). One specific example of using this method to find inhibitors of a particular ATPase has been patented (U.S. Pat. No. 5,759,795).

The effect of the test compound on the extent of binding between a test compound and bimC is identified as effective if its effect on the extent of binding, rate of ATP hydrolysis, or the like is above a threshold level (e.g., a several-fold difference in binding level between control and experimental samples).

Figure 13:
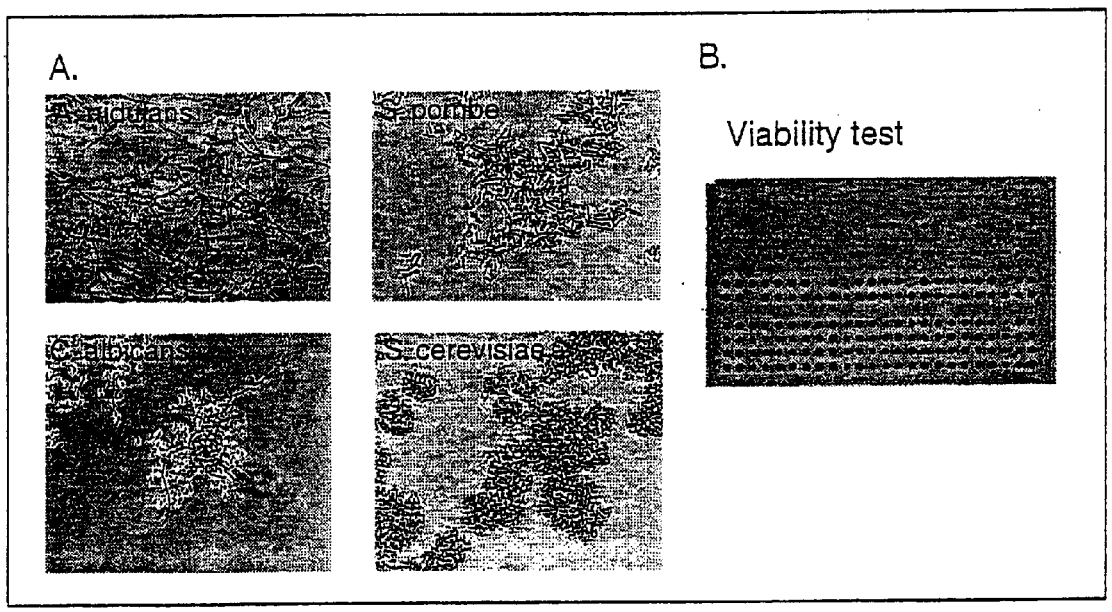
FIG. 13, panel A shows cultures of four (S. cerevisae, S. pombe, C. albicans, and A. nidulans) after 2 day incubation in 25 µl volumes at 25° C. In general, fungi are grown by seeding 100–500 µl of each strain into 25 µl of media and incubated at 25° C. for 2–3 days. Compound effects can be monitored microscopically, by Optical density and/or by treatment with the fluorescent viability stain FUN-1 which changes its fluorescence emission based on the metabolic state of the cell. Viability is ascertained by using a 384 pin replicator to transfer approx. 1 µl of cell suspension onto the appropriate solid media and determining the number of colony forming units. Panel B shows the viability of S. cerevisiae cultures after treatment with dilutions of several compounds from a representative biochemical screen.

For testing the effects of any inhibitors identified in the above biochemical screens, conditions have been defined that allow the assaying of growth defects on a panel of fungal reference strains in a 384 well format. These experiments can be carried out by seeding small numbers of yeast (100–500 cells/well) in a 25 µl volume/well (FIG. 13). Growth is measured microscopically over time as well as by optical density and viability staining. To determine if the inhibitors are fungicidal or fungistatic, dilutions of treated cells can be prepared in 384 well plates and then transferred to solid media using a 384-pin replicator (FIG. 13).

IV. Compounds Suitable for Screening

Candidate agents encompass numerous chemical classes, though typically they are organic molecules, preferably small organic molecules having a molecular weight of more than 100 and less than about 2,500 daltons. Candidate agents are obtained from a wide variety of sources including libraries of synthetic or natural compounds. They include peptides, macromolecules, small molecules, chemical and/ or biological mixtures, and fungal, bacterial, or algal extracts. Such compounds, or molecules, may be either biological, synthetic organic, or even inorganic compounds, and may be obtained from several sources, including pharmaceutical companies and specialty suppliers of libraries (e.g., combinatorial libraries) of compounds.

Methods of the present invention are well suited for screening libraries of compounds in multiwell plates (e.g., 96-, 384-, or higher density well plates), with a different test compound in each well. In particular, the methods may be employed with combinatorial libraries. A variety of combinatorial libraries of random-sequence oligonucleotides, polypeptides, or synthetic oligomers have been proposed. A number of small-molecule libraries have also been developed.

Combinatorial libraries may be formed by a variety of solution-phase or solid-phase methods in which mixtures of different subunits are added stepwise to growing oligomers or parent compounds, until a desired compound is synthesized. A library of increasing complexity can be formed in this manner, for example, by pooling multiple choices of reagents with each additional subunit step.

The identity of library compounds with desired effects on the target protein can be determined by conventional means, such as iterative synthesis methods in which sublibraries containing known residues in one subunit position only are identified as containing active compounds.

Compounds having the following characteristics have been identified using the methods of the invention: $IC_{50}$ values between 15 and 50 µM; low mammalian cellular toxicity ($GI_{50}$>100 µM); and modest fungicidal activity (3–50 µM) against *Aspergillus nidulans* and *Saccharomyces cerevisiae*. (See FIG. 14).

V. Applications

In a preferred embodiment, the candidate agents modulate bimC. In a particularly preferred embodiment, the candidate agent can be used, for example, to inhibit the growth or spread of fungi, mold, fruit flies, etc. Fungi as used herein includes yeasts, mildews, and rusts. Preferred candidate agents are identified which cause cell death selectively on fungi or insects.

Generally, the compositions and methods provided herein are directed at preventing and treating infections caused by Chytridiomycetes, Hyphochrytridiomycetes, Plasmodiophoromycetes, Oomycetes, Zygomycetes, Ascomycetes, and Basidiomycetes. Fungal infections which can be inhibited or treated with compositions provided herein include but are not limited to: Candidiasis including but not limited to onchomycosis, chronic mucocutaneous candidiasis, oral candidiasis, epiglottistis, esophagitis, gastrointestinal infections, genitourinary infections, for example, caused by any Candida species, including but not limited to *Candida albicans, Candida tropicalis, Candida* (*Torulopsis*) *glabrata, Candida parapsilosis, Candida lusitaneae, Candida rugosa* and *Candida pseudotropicalis*; Aspergillosis including but not limited to granulocytopenia caused for example, by, *Aspergillus spp.* including but not limited to *A. fumigatus, Aspergillus favus, Aspergillus niger* and *Aspergillus terreus*; Zygomycosis, including but not limited to pulmonary, sinus and rhinocerebral infections caused by, for example, zygomycetes such as Mucor, Rhizopus spp., *Absidia, Rhizomucor, Cunningamella, Saksenaea, Basidobolus* and *Conidobolus*; Cryptococcosis, including but not limited to infections of the central nervous system—meningitis and infections of the respiratory tract caused by, for example, *Cryptococcus neoformans*; Trichosporonosis caused by, for example, *Trichosporon beigelii*; Pseudallescheriasis caused by, for example, *Pseudallescheria boydii*; Fusarium infection caused by, for example, Fusarium such as *Fusarium solani, Fusarium moniliforme* and *Fusarium proliferartum*; and other infections such as those caused by, for example, Penicillium spp. (generalized subcutaneous abscesses), *Drechslera, Bipolaris, Exserohilum spp., Paecilomyces lilacinum, Exophila jeanselmei* (cutaneous nodules), *Malassezia furfur* (folliculitis), Alternaria (cutaneous nodular lesions), *Aureobasidium pullulans* (splenic and disseminated infection), *Rhodotorula spp.* (disseminated infection), *Chaetomium spp.* (empyema), *Torulopsis candida* (fungemia), *Curvularia spp.* (nasopharyngeal infection), Cunninghamella spp. (pneumonia), *H. Capsulatum, B. dermatitidis, Coccidioides immitis, Sporothrix schenckii* and *Paracoccidioides brasiliensis, Geotrichum candidum* (disseminated infection).

Treating "fungal infections" as used herein refers to the treatment of conditions resulting from fungal infections. Therefore, one may treat, for example, pneumonia, nasopharnygeal infections, disseminated infections and other conditions listed above and known in the art by using the compositions provided herein. In preferred embodiments, treatments and sanitization of areas with the compositions provided herein are provided to immunocompromised patients or areas where there are such patients. Wherein it is desired to identify the particular fungi resulting in the infection, techniques known in the art may be used, see, for example, Musial et al., Clin. Microbiol. Rev., American Society for Microbiology, 349–64 (1998), incorporated herein by reference.

One of skill in the art will readily appreciate that the methods described herein also can be used for diagnostic applications. A diagnostic as used herein is a compound or method that assists in the identification and characterization of a health or disease state in humans or other animals. As described above, bimC is a useful diagnostic tool in vitro for identifying fungal infections.

The present invention also provides for kits for screening for modulators of bimC. Such kits can be prepared from readily available materials and reagents. For example, such kits can comprise any one or more of the following materials: biologically active bimC or a fragment or homolog thereof; reaction tubes; and instructions for testing bimC activity. A wide variety of kits and components can be prepared according to the present invention, depending upon the intended user of the kit and the particular needs of that user.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. A method of identifying a candidate agent as a modulator of function of a tar herein said target protein comprises a protein selected from the group consisting of *Schizosaccharomyces pombe* Cut7; *Saccharomyces cerevisiae* CIN8; and *Saccharomyces cerevisiae* KIP1; or a fragment of said target protein and said method comprises:
   a) adding a candidate agent to a mixture comprising said target protein that directly or indirectly produces ADP or phosphate under conditions which normally allow the production of ADP or phosphate;
   b) subjecting the mixture to an enzymatic reaction that uses said ADP or phosphate as a substrate under conditions which normally allow the ADP or phosphate to be utilized; and
   c) determining the level of activity of the enzymatic reaction wherein a change in said level between the presence and absence of said candidate agent indicates a modulator of said target protein function.

2. The method of claim 1, wherein said determining occurs by a fluorescent, luminescent, radioactive, or absorbance readout.

3. The method of claim 1, wherein said level of activity of said enzymatic reaction is determined at multiple time points.

4. The method of claim 1, wherein a plurality of candidate agents are added.

5. The method of claim 1, wherein said target protein directly produces phosphate or ADP.

6. The method of claim 1, wherein said target protein comprises the motor domain of said target protein.

7. The method of claim 1, wherein said method further comprises the steps of:
   d) culturing one or more cells;
   e) adding said candidate agent to said cells; and
   f) determining the effect of said candidate agent on said cells.

8. The method of claim 7, wherein said cells are selected from the group consisting of *S. cerevisiae, S. pombe, C. albicans,* and *A. nidulans*.

9. The method of claim 1, wherein said culturing step is conducted in a stationary multiwell plate.

10. The method of claim 9, wherein the multiwell plate is a 384-well microtiter plate.

* * * * *

SEQUENCE LISTING

<160> NUMBER OF SEQ ID NOS: 10

<210> SEQ ID NO 1
<211> LENGTH: 4014
<212> TYPE: DNA
<213> ORGANISM: A.nidulans

<400> SEQUENCE: 1

```
ttttctggcc aacggaacaa cagccgacaa ccacgacatt ttgcgacacc gcccctcagc      60
gagactcatt gcttatttac tgagtttggt cttatgtcca attattgttt ctgtacctaa     120
ttcctaccgt catttcacat catggccggc ccccagcggg ctacttatgg ccttgggacc     180
aggcgaacga cgacgcgaca gccgacacga cgggcgggtt ctgcgatacc agaacgccag     240
acatccacag catccccagc tgtatcaaca aaaacggctg ccattagtcg gacgcgcaca     300
ttaaaatccc cgggcgaacc ggcgagcgtg ctcgcgaagc gaaaggagag ggacattgag     360
```

```
cgagaaatca acgaagatac aagcatccat gtcgtcgtac gatgtcgagg ccgtaacgag    420
cgcgaagtca aggagaacag cggggttgtt ttgcagacag agggcgtgaa gggtaaaact    480
gtggagttgt caatgggtcc aaatgcagta tcaaacaaga cctacacgtt cgataaagtc    540
ttctccgcgg cggcagacca aattacggta tacgaggatg tagttctgcc aattgtcact    600
gagatgcttg ctggatacaa ttgcaccatc ttcgcatacg acaaaccgga taccggaaag    660
acatacacga tgtctggaga tatgacggat acattgggta tattatccga caatgctgga    720
attatccccc gcgttctata ttctctattc gccaaattag ctgatacaga gagtacggta    780
aaatgctcct ttatcgagct ttacaacgag gaactccgag atttgctctc cgcggaagag    840
aacccgaagc taaagattta cgacaatgag cagaaaaaag gtcatatgag cacactcgta    900
caaggcatgg aggagacata catcgattcc gcgactgcag gtatcaaact tctccagcaa    960
ggtagccata agcgtcaagt tgctgcgacc aagtgcaacg acctgagttc acgaagtcat   1020
accgtgttca ccatcacggt gaatatcaag cggactacag agtctgggga ggaatacgtg   1080
tgccctggca agctaaacct ggtcgatctg gctggtagcg agaacattgg gcggagcggt   1140
gcagaaaata agcgtgcaac tgaggctggc ttaattaaca agagtctgct taccccttggc  1200 cgcgtgatca atgccctcgt cgacaagagc caacacattc cctatagaga atctaagctc   1260
acgcgcttac ttcaagattc cctcggcgga cgaaccaaga catgcatcat agctacaatg   1320
tcgcctgcta gaagcaatct agaggagaca atttcaacgc tggactatgc tttcagagcc   1380
aagaatatcc gcaacaagcc gcaaataaac tctaccatgc ctaaaatgac gcttctccgt   1440
gaattcactg ccgaaattga gaactaaagg gcggagttga tcgcgaccag acatcgtaac   1500
ggagtgtaca tgtcagtgga atcttatgag gaaatgaaga tggaaaacga gtcacgaagg   1560
attatcagtg aggagcaacg ggccaaaatc gagtcgatgg agtctagcct tcgccataag   1620
gtccaagagt tactcacttt gacgagcaag ttcaacgacc tgaagaagga caacgacgac   1680
acattggccg ctttatgctc cacaaatgat gtcctccaac agaccgacat tgtcttgcag   1740
aacacccgtg cccagcttga gaggaagag atgctgcgat gtgcgcatga agagactgaa    1800
caccagctcc aggatgtcgg caaggactt atatcaaccc ttggccaaac cgttgaagat    1860
attaatagcc tacaatcaaa gcttgatcgg aaagccgagt tggacgctac caatgcggaa   1920
ttatggagag cttcctcaac ggaggtttca gatgtcacga agcggattga ccagcgggtt   1980
gaggctttcc agacgcggca tgcaaagctt ctcgaaacca cgtctgtcaa agttaacgag   2040
ttcattgcta cagagatttc taacatcgag aggactcggt cagatctctc cgagtataac   2100
cgctcgcttg atgcggcatg taacaatgcg aaggctgaga catctagtgc tcacgaagac   2160
atgaacaatg tgcttgaaga aatcaaagat ctgcgcgagg aagtcaagtc taaagtagga   2220
gagggactta atggcctctc agctgccgca gcccggatat cggaggaggt tattggtgaa   2280
ttcacccaac ttcacagcca actgcacaca tccttcaata accttggaaa agacctgaaa   2340
tcgatctttg agacgatggc cacgcatctt tcagagcaga gaacgaaat aaacaggcta    2400 cgggccgagc tacagagctc gaaccgccag aacatagaaa cgacgcacaa ggcctccgct   2460
catctcgctc aagcgattga agaagaacac gtcgctgcgg aagcggaacg tgagatttta   2520
atgtcacaga tcaaagcgct ggttgaggaa tctcgccaga agcaattcgc ccgcctcagg   2580
gccaagatta acggggtcag gaccgagatt tcagcatcag gggacatgtt agagcaggcc   2640
acaactcagc atgaccgcca gatcgatgag tgggttttca agtctgagca attcgctaag   2700
```

-continued

```
gatgtcaatg catcgaaaga tgagatcagg acgaagctgc aaaatgattg ggaggcattt    2760
gatcagcgga attcgacaat ccggaaggca acagaatctg tccataagga gacggtacgc    2820
attgttgacg ttcaagtaga cgacatggga cggcaaatgg aagctctgga cgatttcgtg    2880
gcaaaggcac gatctcagaa tggtcgttac cgtgatgcgc atattgcaac cctggataca    2940
atagccaccg tgttcgcga ctcctactcc tcgattgagg gcgggttga aaacttgact      3000 ggccggatga accagttcca acaagaagca acccatcatc atgccactct ggaagaatcc    3060
attgctccgc tatcaaacga tgttaggaag ccccttacgg acttgtcttc cagttttcaa    3120
aatcgttctc tggaggagta tgtcgccact ggtgtcaccc cgaagaaacg gaagtacgac    3180
tatatttctg tcttgcctag cacggagtct catgaggtcc tcaagtctcg cctgagaaca    3240
acaaaggaga tggaagtcct tccattcaac agcgacgacc agttgtccgg cccttccagc    3300
tctcccggag ttctccgtc gaaaggcttc gtttacaatg acgtcgagga cgaggtagga    3360
actcatgcac caaccgtgac caacgtcaac ccttccaaca ctggacttag ggaagtcgat    3420
gcaaacgtcg ccgcaagacc gctcgtgtat agcacgggcg agaaatccac ggaccaggat    3480
ggttccccag ttgtcagccc ggatagcgcg acagaagcag aagggatgaa cggaccacca    3540
tccaaaaggc gacgctcaaa ttcagttgtt gctgatacta agttgccaaa caagatgctc    3600
gctaggagga tggctggcat gatggagggg agggaaaacg ttccgcctcc tggtatttcc    3660
aatgggcgcc gactgagggg gcgaccttcg ccctgatata ctcttcactc ggacgagttg    3720
attttctcac cgcgaagtat acttataccc tattgctttt ctcgaggtca tgggtttggc    3780
gttctgggaa caatgagatc tgtatcgggc ttttgataga tcgcatatga tacatcgtct    3840
tcgaaagggt tgggtgcttt ttttttttt tgatcggatt tgttgggcat gtgttttgg     3900 gtccggtgtg ggcttctctt ctaccaacat gatgtctggc atccttgaga taccttttt    3960 gtttagtcgg gctacgattt tgacctagat acttttacct atctccgggg aatt          4014
```

<210> SEQ ID NO 2
<211> LENGTH: 1184
<212> TYPE: PRT
<213> ORGANISM: A. nidulans

<400> SEQUENCE: 2

```
Met Ala Gly Pro Gln Arg Ala Thr Tyr Gly Leu Gly Thr Arg Arg Thr
 1               5                  10                  15

Thr Thr Arg Gln Pro Thr Arg Arg Ala Gly Ser Ala Ile Pro Glu Arg
            20                  25                  30

Gln Thr Ser Thr Ala Ser Pro Ala Val Ser Thr Lys Thr Ala Ala Ile
        35                  40                  45

Ser Arg Thr Arg Thr Leu Lys Ser Pro Gly Glu Pro Ala Ser Val Leu
    50                  55                  60

Ala Lys Arg Lys Glu Arg Asp Ile Glu Arg Ile Asn Glu Asp Thr
65                  70                  75                  80

Ser Ile His Val Val Arg Cys Arg Gly Arg Asn Glu Arg Glu Val
                85                  90                  95

Lys Glu Asn Ser Gly Val Val Leu Gln Thr Glu Gly Val Lys Gly Lys
            100                 105                 110

Thr Val Glu Leu Ser Met Gly Pro Asn Ala Val Ser Asn Lys Thr Tyr
        115                 120                 125

Thr Phe Asp Lys Val Phe Ser Ala Ala Asp Gln Ile Thr Val Tyr
    130                 135                 140
```

```
Glu Asp Val Val Leu Pro Ile Val Thr Glu Met Leu Ala Gly Tyr Asn
145                 150                 155                 160

Cys Thr Ile Phe Ala Tyr Gly Gln Thr Gly Thr Gly Lys Thr Tyr Thr
                165                 170                 175

Met Ser Gly Asp Met Thr Asp Thr Leu Gly Ile Leu Ser Asp Asn Ala
            180                 185                 190

Gly Ile Ile Pro Arg Val Leu Tyr Ser Leu Phe Ala Lys Leu Ala Asp
        195                 200                 205

Thr Glu Ser Thr Val Lys Cys Ser Phe Ile Glu Leu Tyr Asn Glu Glu
    210                 215                 220

Leu Arg Asp Leu Leu Ser Ala Glu Glu Asn Pro Lys Leu Lys Ile Tyr
225                 230                 235                 240

Asp Asn Glu Gln Lys Lys Gly His Met Ser Thr Leu Val Gln Gly Met
                245                 250                 255

Glu Glu Thr Tyr Ile Asp Ser Ala Thr Ala Gly Ile Lys Leu Leu Gln
            260                 265                 270

Gln Gly Ser His Lys Arg Gln Val Ala Ala Thr Lys Cys Asn Asp Leu
        275                 280                 285

Ser Ser Arg Ser His Thr Val Phe Thr Ile Thr Val Asn Ile Lys Arg
    290                 295                 300

Thr Thr Glu Ser Gly Glu Glu Tyr Val Cys Pro Gly Lys Leu Asn Leu
305                 310                 315                 320

Val Asp Leu Ala Gly Ser Glu Asn Ile Gly Arg Ser Gly Ala Glu Asn
                325                 330                 335

Lys Arg Ala Thr Glu Ala Gly Leu Ile Asn Lys Ser Leu Leu Thr Leu
            340                 345                 350

Gly Arg Val Ile Asn Ala Leu Val Asp Lys Ser Gln His Ile Pro Tyr
        355                 360                 365

Arg Glu Ser Lys Leu Thr Arg Leu Leu Gln Asp Ser Leu Gly Gly Arg
    370                 375                 380

Thr Lys Thr Cys Ile Ile Ala Thr Met Ser Pro Ala Arg Ser Asn Leu
385                 390                 395                 400

Glu Glu Thr Ile Ser Thr Leu Asp Tyr Ala Phe Arg Ala Lys Asn Ile
                405                 410                 415

Arg Asn Lys Pro Gln Ile Asn Ser Thr Met Pro Lys Met Thr Leu Leu
            420                 425                 430

Arg Glu Phe Thr Ala Glu Ile Glu Lys Leu Lys Ala Glu Leu Ile Ala
        435                 440                 445

Thr Arg His Arg Asn Gly Val Tyr Met Ser Val Glu Ser Tyr Glu Glu
    450                 455                 460

Met Lys Met Glu Asn Glu Ser Arg Arg Ile Ile Ser Glu Glu Gln Arg
465                 470                 475                 480

Ala Lys Ile Glu Ser Met Glu Ser Ser Leu Arg His Lys Val Gln Glu
                485                 490                 495

Leu Leu Thr Leu Thr Ser Lys Phe Asn Asp Leu Lys Lys Asp Asn Asp
            500                 505                 510

Asp Thr Leu Ala Ala Leu Cys Ser Thr Asn Asp Val Leu Gln Gln Thr
        515                 520                 525

Asp Ile Val Leu Gln Asn Thr Arg Ala Gln Leu Glu Glu Glu Glu Met
    530                 535                 540

Leu Arg Cys Ala His Glu Glu Thr Glu His Gln Leu Gln Asp Val Gly
545                 550                 555                 560

Lys Gly Leu Ile Ser Thr Leu Gly Gln Thr Val Glu Asp Ile Asn Ser
```

-continued

```
                    565                 570                 575
Leu Gln Ser Lys Leu Asp Arg Lys Ala Glu Leu Asp Ala Thr Asn Ala
                580                 585                 590
Glu Leu Trp Arg Ala Ser Ser Thr Glu Val Ser Asp Val Thr Lys Arg
            595                 600                 605
Ile Asp Gln Arg Val Glu Ala Phe Gln Thr Arg His Ala Lys Leu Leu
        610                 615                 620
Glu Thr Thr Ser Val Lys Val Asn Glu Phe Ile Ala Thr Glu Ile Ser
625                 630                 635                 640
Asn Ile Glu Arg Thr Arg Ser Asp Leu Ser Glu Tyr Asn Arg Ser Leu
                645                 650                 655
Asp Ala Ala Cys Asn Asn Ala Lys Ala Glu Thr Ser Ser Ala His Glu
            660                 665                 670
Asp Met Asn Asn Val Leu Glu Glu Ile Lys Asp Leu Arg Glu Glu Val
        675                 680                 685
Lys Ser Lys Val Gly Glu Gly Leu Asn Gly Leu Ser Ala Ala Ala Ala
        690                 695                 700
Arg Ile Ser Glu Glu Val Ile Gly Glu Phe Thr Gln Leu His Ser Gln
705                 710                 715                 720
Leu His Thr Ser Phe Asn Asn Leu Gly Lys Asp Leu Lys Ser Ile Phe
                725                 730                 735
Glu Thr Met Ala Thr His Leu Ser Glu Gln Lys Asn Glu Ile Asn Arg
            740                 745                 750
Leu Arg Ala Glu Leu Gln Ser Ser Asn Arg Gln Asn Ile Glu Thr Thr
        755                 760                 765
His Lys Ala Ser Ala His Leu Ala Gln Ala Ile Glu Glu His Val
        770                 775                 780
Ala Ala Glu Ala Glu Arg Glu Ile Leu Met Ser Gln Ile Lys Ala Leu
785                 790                 795                 800
Val Glu Glu Ser Arg Gln Lys Gln Phe Ala Arg Leu Arg Ala Lys Ile
                805                 810                 815
Asp Gly Val Arg Thr Glu Ile Ser Ala Ser Gly Asp Met Leu Glu Gln
            820                 825                 830
Ala Thr Thr Gln His Asp Arg Gln Ile Asp Glu Trp Val Phe Lys Ser
        835                 840                 845
Glu Gln Phe Ala Lys Asp Val Asn Ala Ser Lys Asp Glu Ile Arg Thr
        850                 855                 860
Lys Leu Gln Asn Asp Trp Glu Ala Phe Asp Gln Arg Asn Ser Thr Ile
865                 870                 875                 880
Arg Lys Ala Thr Glu Ser Val His Lys Glu Thr Val Arg Ile Val Asp
                885                 890                 895
Val Gln Val Asp Asp Met Gly Arg Gln Met Glu Ala Leu Asp Asp Phe
            900                 905                 910
Val Ala Lys Ala Arg Ser Gln Asn Gly Arg Tyr Arg Asp Ala His Ile
        915                 920                 925
Ala Thr Leu Asp Thr Ile Ala Thr Gly Val Arg Asp Ser Tyr Ser Ser
        930                 935                 940
Ile Glu Gly Arg Val Glu Asn Leu Thr Gly Arg Met Asn Gln Phe Gln
945                 950                 955                 960
Gln Glu Ala Thr His His His Ala Thr Leu Glu Glu Ser Ile Ala Pro
                965                 970                 975
Leu Ser Asn Asp Val Arg Lys Pro Leu Thr Asp Leu Ser Ser Ser Phe
            980                 985                 990
```

```
Gln Asn Arg Ser Leu Glu Glu Tyr Val Ala Thr Gly Val Thr Pro Lys
        995                 1000                1005
Lys Arg Lys Tyr Asp Tyr Ile Ser Val Leu Pro Ser Thr Glu Ser His
    1010                1015                1020
Glu Val Leu Lys Ser Arg Leu Arg Thr Thr Lys Glu Met Glu Val Leu
1025                1030                1035                1040
Pro Phe Asn Ser Asp Asp Gln Leu Ser Gly Pro Ser Ser Ser Pro Gly
                1045                1050                1055
Gly Ser Pro Ser Lys Gly Phe Val Tyr Asn Asp Val Glu Asp Glu Val
                1060                1065                1070
Gly Thr His Ala Pro Thr Val Thr Asn Val Asn Pro Ser Asn Thr Gly
                1075                1080                1085
Leu Arg Glu Val Asp Ala Asn Val Ala Ala Arg Pro Leu Val Tyr Ser
    1090                1095                1100
Thr Gly Glu Lys Ser Thr Asp Gln Asp Gly Ser Pro Val Ser Pro
1105                1110                1115                1120
Asp Ser Ala Thr Glu Ala Glu Gly Met Asn Gly Pro Pro Ser Lys Arg
                1125                1130                1135
Arg Arg Ser Asn Ser Val Val Ala Asp Thr Lys Leu Pro Asn Lys Met
            1140                1145                1150
Leu Ala Arg Arg Met Ala Gly Met Met Glu Gly Arg Glu Asn Val Pro
            1155                1160                1165
Pro Pro Gly Ile Ser Asn Gly Arg Arg Leu Arg Gly Arg Pro Ser Pro
        1170                1175                1180

<210> SEQ ID NO 3
<211> LENGTH: 3884
<212> TYPE: DNA
<213> ORGANISM: Saccharomyces cerevisiae

<400> SEQUENCE: 3
aagcaagaat tgaacatgga tgaattcatt ggatcaaaga ccgatttaat caaagatcaa      60
gtgagagata ttcttgataa attgaatatt atttaattct tcatttagaa aaatttcagc    120
tgctttttt tttcttttc tttccttagg cgtctcgagg ttacaagtcg gagtccctct     180
tcactatcgt ttgtccactt tttttatatc cccattattt tcaatctgaa tttcattttt    240
ttttttaat tcatgaaatt tatatgtccc acgtattact acatatttgc gtttttaatt     300
aaataaataa ctgttacttt tattatatct tatttgcaga tcacttatct gatcaaatgt    360
tttcgttttc gtgtgtggtg acgatgtatt aggtacgcga aataaacaaa acaaacaaac    420
aaggccgcaa caataacatc atctaaagac ttcctttgtg acccgcttct caacagcggg    480
tgtagaactt atggtatggc cagaaagtaa cgttgagtat agatacagaa gcaagcaatt    540
caaaggaaaa agtaataaaa agtatataaa agcgcaaaaa atacaacaag aaagaatttg    600
tttgatgcca gcggaaaacc aaaatacggg tcaagataga agctccaaca gcatcagtaa    660
aaatggcaac tctcaggttg gatgtcacac tgttcctaat gaggaactga acatcactgt    720
agctgtgcga tgcagaggaa ggaatgaaag ggaaattagt atgaaaagct ccgttgtggt    780
aaatgttcca gatattacag gttctaaaga aatttccatt aacacgacgg gagataccgg    840
tataactgct caaatgaatg ccaagagata cacagtggac aaagtcttcg gtcccggcgc    900
ttcccaggat ctaattttg atgaagtggc gggcccatta ttccaggatt tcattaaagg    960
ttacaattgc accgtactgg tatatggtat gacgtcaaca ggtaaaacat atacaatgac   1020
```

-continued

| | |
|---|---|
| gggcgacgaa aagttatata atggtgaatt gagcgatgca gcaggaatta taccgagggt | 1080 |
| tcttttgaag ttgtttgaca cattggaact acaacagaac gattacgtag taaaatgttc | 1140 |
| gttcattgaa ctctcaacg aagaattgaa ggacctcttg dacagcaata gcaacggctc | 1200 |
| tagtaatact ggctttgacg gccaatttat gaaaaaattg aggattttg cttcaagcac | 1260 |
| agcaaataat accactagca acagtgctag tagttccagg agtaattcta ggaacagttc | 1320 |
| tccgaggtca ttaaatgatc taacacctaa agctgctcta ttaagaaaaa ggttaaggac | 1380 |
| aaaatcactg ccgaatacca tcaagcaaca gtatcaacaa caacaggcag tgaattccag | 1440 |
| gaacaactct tcctctaact ctggctctac cactaataat gcttctagta acaccaacac | 1500 |
| aaataacggt caaagaagtt cgatggctcc aaatgaccaa actaatggta tatacatcca | 1560 |
| gaatttgcaa gaatttcaca taacaaatgc tatggagggg ctaaacctat tacaaaaagg | 1620 |
| cttaaagcat aggcaagtag cgtccactaa aatgaacgat ttttccagta gatctcatac | 1680 |
| catttttaca atcactttgt ataagaagca tcaggatgaa ctatttagaa tttccaaaat | 1740 |
| gaatcttgtg gatttagctg gttcagaaaa catcaacaga tccggagcat taaatcaacg | 1800 |
| tgccaaagaa gctggttcaa tcaaccaaag tctattgacg ctgggcaggg tcataaacgc | 1860 |
| actcgtagat aaaagcggcc atataccttt ccgtgaatcg aaattgaccc gcctgcttca | 1920 |
| agattccctg ggtggtaata cgaaaaccgc actaattgct actatatcgc ctgcaaaggt | 1980 |
| aacttctgaa gaaacctgca gtacattaga gtatgcttcg aaggctaaaa acattaagaa | 2040 |
| caagccgcaa ctgggttcat ttataatgaa ggatattttg gttaaaaata taactatgga | 2100 |
| attagcaaag attaaatccg atttactctc tacaaagtcc aaagaaggaa tatatatgag | 2160 |
| ccaagatcac tacaaaaatt tgaacagtga tttagaaagt tataaaaatg aagttcaaga | 2220 |
| atgtaaaaga gaaattgaaa gtttgacatc gaaaaatgca ttgctagtaa aagataaatt | 2280 |
| gaagtcaaaa gaaactattc aatctcaaaa ttgccaaata gaatcattga aaactaccat | 2340 |
| agatcattta agggcacaac tagataaaca gcataaaact gaaattgaaa tatccgattt | 2400 |
| taataacaaa ctacagaagt tgactgaggt aatgcaaatg gccctacatg attacaaaaa | 2460 |
| aagagaactt gaccttaatc aaaagtttga aatgcatatt actaaagaaa ttaaaaaatt | 2520 |
| gaaatctaca ctgtttttac aattaaacac tatgcaacag gaaagtattc ttcaagagac | 2580 |
| taatatccaa ccaaatcttg atatgatcaa aaatgaagta ctgactctta tgagaaccat | 2640 |
| gcaagaaaaa gctgaactaa tgtacaaaga ctgtgtgaag aaaatttttaa acgaatctcc | 2700 |
| taaattcttc aatgttgtta ttgagaaaat cgacataata agagtagatt tccaaaaatt | 2760 |
| ttataaaaat atagccgaga atctttctga tattagcgaa gaaaataaca acatgaaaca | 2820 |
| gtacttaaaa aaccattttt tcaagaataa ccatcaagaa ttactgaatc gtcatgtgga | 2880 |
| ttctacttat gaaatatttg agaagagaac aaacgagttt gttgagaact ttaaaaaggt | 2940 |
| cctaaatgac caccttgacg aaaataaaaa actaataatg cacaatctga caactgcaac | 3000 |
| cagcgcggtt attgatcaag aaatggatct gtttgaaccc aagcgcgtta atgggaaaa | 3060 |
| ttcatttgat ctgataaatg attgtgactc catgaataac gaattctata atagcatggc | 3120 |
| agcgacgcta tcgcaaatca agagtactgt tgatacatca tcaaattcga tgaatgagtc | 3180 |
| tatttcagtc atgaaaggac aagtggaaga atcggagaac gctatatccc ttttgaagaa | 3240 |
| caataccaaa tttaatgatc aatttgagca gcttattaac aagcataaca tgttgaaaga | 3300 |
| taacattaaa aattcgataa catcaacaca ctctcatata actaatgtgg atgatatcta | 3360 |
| taatacgatt gaaaacataa tgaaaaacta tggtaacaag gaaaacgcta ccaaagacga | 3420 |

-continued

```
aatgatcgag aacatattga aggaaatacc aaatctaagt aagaaaatgc cgttaaggtt    3480
atcaaacata aatagcaatt cagtgcaaag tgtaatatcg cccaaaaagc atgcaattga    3540
agatgaaaac aaatccagtg aaaatgtgga caatgagggc tcgagaaaaa tgttaaagat    3600
tgaatagttg atattgcctt tcagtcgaat atatattcaa actagtggtt aataaaaaca    3660
aagtatgtaa agaatactca gttattcatt agaaggcaag acagaagaga agggtgtgaa    3720
accacctcta ccaaacacac caagagatga acctaaatca aattttcaca gagctaacta    3780
tataaacgtt tggattcgtg tgtactatct ttatttacgg aaataagttg taatattaaa    3840
aaaaaaaaaa aacattttga tggacaatga atttctctaa tttt                    3884
```

<210> SEQ ID NO 4
<211> LENGTH: 1038
<212> TYPE: PRT
<213> ORGANISM: Saccharomyces cerevisiae

<400> SEQUENCE: 4

```
Met Val Trp Pro Glu Ser Asn Val Glu Tyr Arg Tyr Arg Ser Lys Gln
 1               5                  10                  15

Phe Lys Gly Lys Ser Asn Lys Lys Tyr Ile Lys Ala Gln Lys Ile Gln
            20                  25                  30

Gln Glu Arg Ile Cys Leu Met Pro Ala Glu Asn Gln Asn Thr Gly Gln
        35                  40                  45

Asp Arg Ser Ser Asn Ser Ile Ser Lys Asn Gly Asn Ser Gln Val Gly
    50                  55                  60

Cys His Thr Val Pro Asn Glu Glu Leu Asn Ile Thr Val Ala Val Arg
65                  70                  75                  80

Cys Arg Gly Arg Asn Glu Arg Glu Ile Ser Met Lys Ser Ser Val Val
                85                  90                  95

Val Asn Val Pro Asp Ile Thr Gly Ser Lys Glu Ile Ser Ile Asn Thr
            100                 105                 110

Thr Gly Asp Thr Gly Ile Thr Ala Gln Met Asn Ala Lys Arg Tyr Thr
        115                 120                 125

Val Asp Lys Val Phe Gly Pro Gly Ala Ser Gln Asp Leu Ile Phe Asp
    130                 135                 140

Glu Val Ala Gly Pro Leu Phe Gln Asp Phe Ile Lys Gly Tyr Asn Cys
145                 150                 155                 160

Thr Val Leu Val Tyr Gly Met Thr Ser Thr Gly Lys Thr Tyr Thr Met
                165                 170                 175

Thr Gly Asp Glu Lys Leu Tyr Asn Gly Glu Leu Ser Asp Ala Ala Gly
            180                 185                 190

Ile Ile Pro Arg Val Leu Leu Lys Leu Phe Asp Thr Leu Glu Leu Gln
        195                 200                 205

Gln Asn Asp Tyr Val Val Lys Cys Ser Phe Ile Glu Leu Tyr Asn Glu
    210                 215                 220

Glu Leu Lys Asp Leu Leu Asp Ser Asn Ser Asn Gly Ser Ser Asn Thr
225                 230                 235                 240

Gly Phe Asp Gly Gln Phe Met Lys Lys Leu Arg Ile Phe Ala Ser Ser
                245                 250                 255

Thr Ala Asn Asn Thr Thr Ser Asn Ser Ala Ser Ser Arg Ser Asn
            260                 265                 270

Ser Arg Asn Ser Ser Pro Arg Ser Leu Asn Asp Leu Thr Pro Lys Ala
    275                 280                 285
```

```
Ala Leu Leu Arg Lys Arg Leu Arg Thr Lys Ser Leu Pro Asn Thr Ile
            290                 295                 300

Lys Gln Gln Tyr Gln Gln Gln Ala Val Asn Ser Arg Asn Asn Ser
305                 310                 315                 320

Ser Ser Asn Ser Gly Ser Thr Thr Asn Asn Ala Ser Ser Asn Thr Asn
                325                 330                 335

Thr Asn Asn Gly Gln Arg Ser Ser Met Ala Pro Asn Asp Gln Thr Asn
            340                 345                 350

Gly Ile Tyr Ile Gln Asn Leu Gln Glu Phe His Ile Thr Asn Ala Met
                355                 360                 365

Glu Gly Leu Asn Leu Leu Gln Lys Gly Leu Lys His Arg Gln Val Ala
            370                 375                 380

Ser Thr Lys Met Asn Asp Phe Ser Ser Arg Ser His Thr Ile Phe Thr
385                 390                 395                 400

Ile Thr Leu Tyr Lys Lys His Gln Asp Glu Leu Phe Arg Ile Ser Lys
                405                 410                 415

Met Asn Leu Val Asp Leu Ala Gly Ser Glu Asn Ile Asn Arg Ser Gly
            420                 425                 430

Ala Leu Asn Gln Arg Ala Lys Glu Ala Gly Ser Ile Asn Gln Ser Leu
            435                 440                 445

Leu Thr Leu Gly Arg Val Ile Asn Ala Leu Val Asp Lys Ser Gly His
            450                 455                 460

Ile Pro Phe Arg Glu Ser Lys Leu Thr Arg Leu Leu Gln Asp Ser Leu
465                 470                 475                 480

Gly Gly Asn Thr Lys Thr Ala Leu Ile Ala Thr Ile Ser Pro Ala Lys
                485                 490                 495

Val Thr Ser Glu Glu Thr Cys Ser Thr Leu Glu Tyr Ala Ser Lys Ala
            500                 505                 510

Lys Asn Ile Lys Asn Lys Pro Gln Leu Gly Ser Phe Ile Met Lys Asp
            515                 520                 525

Ile Leu Val Lys Asn Ile Thr Met Glu Leu Ala Lys Ile Lys Ser Asp
            530                 535                 540

Leu Leu Ser Thr Lys Ser Lys Glu Gly Ile Tyr Met Ser Gln Asp His
545                 550                 555                 560

Tyr Lys Asn Leu Asn Ser Asp Leu Glu Ser Tyr Lys Asn Glu Val Gln
                565                 570                 575

Glu Cys Lys Arg Glu Ile Glu Ser Leu Thr Ser Lys Asn Ala Leu Leu
            580                 585                 590

Val Lys Asp Lys Leu Lys Ser Lys Glu Thr Ile Gln Ser Gln Asn Cys
            595                 600                 605

Gln Ile Glu Ser Leu Lys Thr Thr Ile Asp His Leu Arg Ala Gln Leu
            610                 615                 620

Asp Lys Gln His Lys Thr Glu Ile Glu Ile Ser Asp Phe Asn Asn Lys
625                 630                 635                 640

Leu Gln Lys Leu Thr Glu Val Met Gln Met Ala Leu His Asp Tyr Lys
                645                 650                 655

Lys Arg Glu Leu Asp Leu Asn Gln Lys Phe Glu Met His Ile Thr Lys
            660                 665                 670

Glu Ile Lys Lys Leu Lys Ser Thr Leu Phe Leu Gln Leu Asn Thr Met
            675                 680                 685

Gln Gln Glu Ser Ile Leu Gln Glu Thr Asn Ile Gln Pro Asn Leu Asp
            690                 695                 700

Met Ile Lys Asn Glu Val Leu Thr Leu Met Arg Thr Met Gln Glu Lys
```

```
                705                 710                 715                 720
Ala Glu Leu Met Tyr Lys Asp Cys Val Lys Lys Ile Leu Asn Glu Ser
                    725                 730                 735
Pro Lys Phe Phe Asn Val Val Ile Glu Lys Ile Asp Ile Ile Arg Val
                    740                 745                 750
Asp Phe Gln Lys Phe Tyr Lys Asn Ile Ala Glu Asn Leu Ser Asp Ile
                    755                 760                 765
Ser Glu Glu Asn Asn Asn Met Lys Gln Tyr Leu Lys Asn His Phe Phe
                    770                 775                 780
Lys Asn Asn His Gln Glu Leu Leu Asn Arg His Val Asp Ser Thr Tyr
785                 790                 795                 800
Glu Asn Ile Glu Lys Arg Thr Asn Glu Phe Val Glu Asn Phe Lys Lys
                    805                 810                 815
Val Leu Asn Asp His Leu Asp Glu Asn Lys Lys Leu Ile Met His Asn
                    820                 825                 830
Leu Thr Thr Ala Thr Ser Ala Val Ile Asp Gln Glu Met Asp Leu Phe
                    835                 840                 845
Glu Pro Lys Arg Val Lys Trp Glu Asn Ser Phe Asp Leu Ile Asn Asp
                    850                 855                 860
Cys Asp Ser Met Asn Asn Glu Phe Tyr Asn Ser Met Ala Ala Thr Leu
865                 870                 875                 880
Ser Gln Ile Lys Ser Thr Val Asp Thr Ser Ser Asn Ser Met Asn Glu
                    885                 890                 895
Ser Ile Ser Val Met Lys Gly Gln Val Glu Ser Glu Asn Ala Ile
                    900                 905                 910
Ser Leu Leu Lys Asn Asn Thr Lys Phe Asn Asp Gln Phe Glu Gln Leu
                    915                 920                 925
Ile Asn Lys His Asn Met Leu Lys Asp Asn Ile Lys Asn Ser Ile Thr
                    930                 935                 940
Ser Thr His Ser His Ile Thr Asn Val Asp Asp Ile Tyr Asn Thr Ile
945                 950                 955                 960
Glu Asn Ile Met Lys Asn Tyr Gly Asn Lys Glu Asn Ala Thr Lys Asp
                    965                 970                 975
Glu Met Ile Glu Asn Ile Leu Lys Glu Ile Pro Asn Leu Ser Lys Lys
                    980                 985                 990
Met Pro Leu Arg Leu Ser Asn Ile Asn Ser Asn Ser Val Gln Ser Val
                    995                 1000                1005
Ile Ser Pro Lys Lys His Ala Ile Glu Asp Glu Asn Lys Ser Ser Glu
        1010                1015                1020
Asn Val Asp Asn Glu Gly Ser Arg Lys Met Leu Lys Ile Glu
1025                1030                1035

<210> SEQ ID NO 5
<211> LENGTH: 4223
<212> TYPE: DNA
<213> ORGANISM: S.pombe

<400> SEQUENCE: 5
aacggaagaa atcttgctgc ttagcttctt cgacaactgg agcaccttcg attactacaa      60
ccgtgtcata tccaacaggt ttagttacat taagcttaac ttccagttca gaaacatcga     120
tttcctcgtc ctttacgacg atttgatcct taatttcctc aattaggatt tcgacatttt     180
ctggtgtagt gccgttgtct ctagtcaagt ttcttcaccc agtgactggg gggacatcga     240
agagtaactt tagagaaatt taaaaaaaat tgaaagtaat gaaaagtaga atttaaaaaa     300
```

```
catggtatca tttaaaataa actaataaag ttgattctgt tttatatttc ttctttttta    360
gattttaact cattctaccg attttgacta ttatcattac tgacaacagt ttatctgcca    420
agttcgttca ttttgtattg attttagta ttagcacaat tgttggattt ttcataaaag    480
ttcttttttc tcctttttat actgttgatt tgtactgcaa acattggaa tgagacattc     540 caagtgttac cgtgtctgag tcctcgttct tgtttacaac aattcaacaa catactcagg   600
agcgaacaat tgtccaattt attcattctt tttaccccta aaacagacg tttacgatct    660 tttcctattt taaatttacc cctttttttt atattgtggt ttattgaact ttacaacaga   720
attgcaattt aaattaacaa ccttgtcgct ttctttgtaa caatccttac tcataaaacc   780
gaatggcccc tagagttgca cctggtggct cacaacaatt tctaggaaag caggggttga   840
aagctaaaaa cccggtttct actccaaatt cacatttccg tctgcgagca atcctaggaa   900
acgacgtgag cctcctacta ttgacactgg gtacccagat cgctccgaca ctaattctcc   960
gacagatcat gcacttcatg atgagaacga accaatatt aacgtagtcg tccgtgttcg    1020
tggtcgtaca gaccaagaag tacgcgacaa tagtagcctt gctgtatcga cttcgggcgc   1080
tatgggtgct gaattggcca tccagtcgga tccttcatcc atgttggtca cgaagacgta   1140
tgcctttgat aaagtctttg gtcctgaagc tgaccagtta atgctattcg aaaattcggt   1200
agcgcccatg ctggagcaag tattgaacgg ctataattgt actatatttg cgtacggaca   1260
aactggaacc ggtaaaacat atactatgtc tggtgatctt agcgattccg atggaatttt   1320
gtctgaagga gcaggcctta ttcctcgtgc cctttatcaa ttattttcct ccttggacaa   1380
cagtaatcaa gaatatgctg tcaaatgctc ctattatgaa ctttacaacg aggaaattcg   1440
cgatcttttg gtttccgaag aattgcgaaa gccagctcgt gtttttgaag atacttcgcg   1500
gagagggaac gttgttatta ctggtattga agaaagttat ataaaaaatg ctggcgatgg   1560
gttgcgattg ttacgtgaag gctctcaccg gcgtcaagtt gctgctacaa agtgtaacga   1620
tctttcatct cgtagtcatt caatcttcac gataactctg catagaaagg tatcttcggg   1680
aatgacagat gaaactaatt cacttaccat aaataataac tctgatgact tgctgcgcgc   1740
cagcaaactt catatggttg atttggctgg aagcgagaac attggacgtt ctggagctga   1800
aaacaaacgt gctcgagaaa ctggaatgat caatcaatca ctattaacat taggccgagt   1860
aattaatgca ttagtggaaa aggcccacca tattccatac cgtgagtcca agcttacacg   1920
cctattgcag gattctttgg ggggaaagac taaaacctct atgatcgtta ccgtatcttc   1980
tactaatact aatttggaag aaacaatttc tactttggag tatgctgctc gtgctaaaag   2040
tatacgcaat aagcctcaaa ataatcagct tgtctttcga aaagtcctta taaaagactt   2100
agtgttagat atcgaacgat tgaaaaatga ccttaatgcc acccgtaaaa agaacggagt   2160
ttatcttgct gaaagcacgt ataaggagct tatggatcgt gttcaaaaca agatttgtt   2220 atgccaggaa caggctcgca aacttgaagt gctggactta aacgttaaaa gttcgaggga   2280
acaactgcag tatgttccta aatctaatca agaacataaa aaggaagttg aagctctgca   2340
actgcaactg gttaattcat ctacagagtt agaaagtgta agtctgaga acgaaaagct    2400 gaaaaatgaa ctagttttag aaatcgaaaa acgaaaaaaa tacgaaacca tgaagctaa    2460 aattacaact gttgcaacag acctttccca atattaccga gaatcaaaag aatacattgc   2520
tagcttatat gagaagcttg atcgcactga acgaaataat aaagaaaatg aaaacaattt   2580
ttggaatctt aagttcaatt tgttaacgat gttgagatct tttcatggaa gtttttactga  2640
```

```
                                              -continued tgaaacaaat ggctatttta ctttgttgaa tgattttaat gcttcaatgg aagaattatt    2700
gaacacccac agtaatcaac tgctgatttc tatgaccaaa attactgagc attttcagag    2760
tttagatgag gcgttgcaaa gtgctcgttc ttcttgtgca gtacctaatt ctagcttaga    2820
cctaattgtt tctgaattaa aggattccaa aaacagcctt cttgatgcgt tggagcacag    2880
tctgcaggat attagcatgt cttcccagaa gttgggaaat ggaatttctt cggaattgat    2940
agaattgcag aaagacatga aagaatcata ccgacaactt gttcaggaat taagatcact    3000 ataatttta cagcatactc atgaagaatc acagaaggag ctaatgtatg gtgtgcgtaa    3060
cgatattgat gctctggtta aaacttgcac aacatctttg aacgatgcag atataatatt    3120
aagtgattac atatctgatc aaaaatccaa atttgaatcc aagcaacaag atttgattgc    3180
taatattggt aaaattgttt caatttttt acaggaacag aacgaatctt tgtataccaa    3240
agcggatatc ttacattcac atctcaatga tacaaactcg aatataagga agcaaacga    3300 aattatgaat aaccgttcag aagagttttt acggaatgcg gcttcacaag cagaaatcgt    3360
gggtgccaat aaagaaagga ttcaaaagac agttgaaaat ggatctcaac tgcttgacag    3420
taaaagcaag gccattcata gcaattccag atcaatgtat gaccattgct ggctttagc    3480 ggagtctcaa aaacaaggtg ttaatcttga agttcaaacg ctggatcgtt gttgcagaa    3540 agtaaaagag cattcagaag ataataccaa ggagaagcat caacaattac ttgatttatt    3600
ggaatccctt gttggcaaca atgacaatct tatcgattcc atcaagacac cgcacactga    3660
attacagaaa attacagatc atgttttaaa gggaacgaca tcacttgcta atcatactaa    3720
tgaattactt ggtttaggag atgaatctct atgtaacctt gaaactacta tagaagacac    3780
gtctttggtg aagctggaaa caactggcga tacaccttcc aaacgagaac ttcctgccac    3840
tccatcttgg acacgagatt cgtctttaat taaggaaact acgaatttaa atttagattc    3900
ggataagaaa ttcgttaggg aaacctacac atcgtctaat caaactaatg agccggacgt    3960
atatgataaa ccatctaatt catcaagaac tagtcttttg cggagtagca gaagtgccta    4020
ttccaaaatg aaacgataat gacacgattt tattaattta tacttaatgg acgaaaatac    4080
aatagaaatg tattacatct tggggctttg gctggttaaa acggaaagtt tggttatgtg    4140
tgtacatact gcgtttttaaa taatagtttt aggagttgta tacatataaa gattaattta    4200
gatagaagtt taatgatata cag                                            4223

<210> SEQ ID NO 6
<211> LENGTH: 1073
<212> TYPE: PRT
<213> ORGANISM: S.pombe

<400> SEQUENCE: 6

Met Ala Pro Arg Val Ala Pro Gly Gly Ser Gln Gln Phe Leu Gly Lys
1               5                   10                  15

Gln Gly Leu Lys Ala Lys Asn Pro Val Ser Thr Pro Asn Ser His Phe
            20                  25                  30

Arg Leu Arg Ala Ile Leu Gly Asn Asp Val Ser Leu Leu Leu Leu Thr
        35                  40                  45

Leu Asp His Ala Leu His Asp Glu Asn Glu Thr Asn Ile Asn Val Val
    50                  55                  60

Val Arg Val Arg Gly Arg Thr Asp Gln Glu Val Arg Asp Asn Ser Ser
65                  70                  75                  80

Leu Ala Val Ser Thr Ser Gly Ala Met Gly Ala Glu Leu Ala Ile Gln
                85                  90                  95
```

```
Ser Asp Pro Ser Ser Met Leu Val Thr Lys Thr Tyr Ala Phe Asp Lys
            100                 105                 110

Val Phe Gly Pro Glu Ala Asp Gln Leu Met Leu Phe Glu Asn Ser Val
            115                 120                 125

Ala Pro Met Leu Glu Gln Val Leu Asn Gly Tyr Asn Cys Thr Ile Phe
            130                 135                 140

Ala Tyr Gly Gln Thr Gly Thr Gly Lys Thr Tyr Thr Met Ser Gly Asp
145                 150                 155                 160

Leu Ser Asp Ser Asp Gly Ile Leu Ser Glu Gly Ala Gly Leu Ile Pro
                    165                 170                 175

Arg Ala Leu Tyr Gln Leu Phe Ser Ser Leu Asp Asn Ser Asn Gln Glu
            180                 185                 190

Tyr Ala Val Lys Cys Ser Tyr Glu Leu Tyr Asn Glu Glu Ile Arg
            195                 200                 205

Asp Leu Leu Val Ser Glu Glu Leu Arg Lys Pro Ala Arg Val Phe Glu
            210                 215                 220

Asp Thr Ser Arg Arg Gly Asn Val Val Ile Thr Gly Ile Glu Glu Ser
225                 230                 235                 240

Tyr Ile Lys Asn Ala Gly Asp Gly Leu Arg Leu Leu Arg Glu Gly Ser
                    245                 250                 255

His Arg Arg Gln Val Ala Ala Thr Lys Cys Asn Asp Leu Ser Ser Arg
            260                 265                 270

Ser His Ser Ile Phe Thr Ile Thr Leu His Arg Lys Val Ser Ser Gly
            275                 280                 285

Met Thr Asp Glu Thr Asn Ser Leu Thr Ile Asn Asn Asn Ser Asp Asp
            290                 295                 300

Leu Leu Arg Ala Ser Lys Leu His Met Val Asp Leu Ala Gly Ser Glu
305                 310                 315                 320

Asn Ile Gly Arg Ser Gly Ala Glu Asn Lys Arg Ala Arg Glu Thr Gly
                    325                 330                 335

Met Ile Asn Gln Ser Leu Leu Thr Leu Gly Arg Val Ile Asn Ala Leu
            340                 345                 350

Val Glu Lys Ala His His Ile Pro Tyr Arg Glu Ser Lys Leu Thr Arg
            355                 360                 365

Leu Leu Gln Asp Ser Leu Gly Gly Lys Thr Lys Thr Ser Met Ile Val
            370                 375                 380

Thr Val Ser Ser Thr Asn Thr Asn Leu Glu Glu Thr Ile Ser Thr Leu
385                 390                 395                 400

Glu Tyr Ala Ala Arg Ala Lys Ser Ile Arg Asn Lys Pro Gln Asn Asn
                    405                 410                 415

Gln Leu Val Phe Arg Lys Val Leu Ile Lys Asp Leu Val Leu Asp Ile
            420                 425                 430

Glu Arg Leu Lys Asn Asp Leu Asn Ala Thr Arg Lys Lys Asn Gly Val
            435                 440                 445

Tyr Leu Ala Glu Ser Thr Tyr Lys Glu Leu Met Asp Arg Val Gln Asn
450                 455                 460

Lys Asp Leu Leu Cys Gln Glu Gln Ala Arg Lys Leu Glu Val Leu Asp
465                 470                 475                 480

Leu Asn Val Lys Ser Ser Arg Glu Gln Leu Gln Tyr Val Ser Lys Ser
                    485                 490                 495

Asn Gln Glu His Lys Lys Glu Val Glu Ala Leu Gln Leu Gln Leu Val
            500                 505                 510
```

-continued

```
Asn Ser Ser Thr Glu Leu Glu Ser Val Lys Ser Glu Asn Glu Lys Leu
        515                 520                 525

Lys Asn Glu Leu Val Leu Glu Ile Glu Lys Arg Lys Lys Tyr Glu Thr
        530                 535                 540

Asn Glu Ala Lys Ile Thr Thr Val Ala Thr Asp Leu Ser Gln Tyr Tyr
545                 550                 555                 560

Arg Glu Ser Lys Glu Tyr Ile Ala Ser Leu Tyr Glu Lys Leu Asp Arg
                565                 570                 575

Thr Glu Arg Asn Asn Lys Glu Asn Glu Asn Asn Phe Trp Asn Leu Lys
            580                 585                 590

Phe Asn Leu Leu Thr Met Leu Arg Ser Phe His Gly Ser Phe Thr Asp
            595                 600                 605

Glu Thr Asn Gly Tyr Phe Thr Leu Leu Asn Asp Phe Asn Ala Ser Met
    610                 615                 620

Glu Glu Leu Leu Asn Thr His Ser Asn Gln Leu Leu Ile Ser Met Thr
625                 630                 635                 640

Lys Ile Thr Glu His Phe Gln Ser Leu Asp Glu Ala Leu Gln Ser Ala
                645                 650                 655

Arg Ser Ser Cys Ala Val Pro Asn Ser Ser Leu Asp Leu Ile Val Ser
            660                 665                 670

Glu Leu Lys Asp Ser Lys Asn Ser Leu Leu Asp Ala Leu Glu His Ser
        675                 680                 685

Leu Gln Asp Ile Ser Met Ser Ser Gln Lys Leu Gly Asn Gly Ile Ser
    690                 695                 700

Ser Glu Leu Ile Glu Leu Gln Lys Asp Met Lys Glu Ser Tyr Arg Gln
705                 710                 715                 720

Leu Val Gln Glu Leu Arg Ser Leu Tyr Asn Leu Gln His Thr His Glu
                725                 730                 735

Glu Ser Gln Lys Glu Leu Met Tyr Gly Val Arg Asn Asp Ile Asp Ala
            740                 745                 750

Leu Val Lys Thr Cys Thr Thr Ser Leu Asn Asp Ala Asp Ile Ile Leu
    755                 760                 765

Ser Asp Tyr Ile Ser Asp Gln Lys Ser Lys Phe Glu Ser Lys Gln Gln
770                 775                 780

Asp Leu Ile Ala Asn Ile Gly Lys Ile Val Ser Asn Phe Leu Gln Glu
785                 790                 795                 800

Gln Asn Glu Ser Leu Tyr Thr Lys Ala Asp Ile Leu His Ser His Leu
                805                 810                 815

Asn Asp Thr Asn Ser Asn Ile Arg Lys Ala Asn Glu Ile Met Asn Asn
            820                 825                 830

Arg Ser Glu Glu Phe Leu Arg Asn Ala Ala Ser Gln Ala Glu Ile Val
    835                 840                 845

Gly Ala Asn Lys Glu Arg Ile Gln Lys Thr Val Glu Asn Gly Ser Gln
850                 855                 860

Leu Leu Asp Ser Lys Ser Lys Ala Ile His Ser Asn Ser Arg Ser Met
865                 870                 875                 880

Tyr Asp His Cys Leu Ala Leu Ala Glu Ser Gln Lys Gln Gly Val Asn
                885                 890                 895

Leu Glu Val Gln Thr Leu Asp Arg Leu Leu Gln Lys Val Lys Glu His
            900                 905                 910

Ser Glu Asp Asn Thr Lys Glu Lys His Gln Gln Leu Leu Asp Leu Leu
    915                 920                 925

Glu Ser Leu Val Gly Asn Asn Asp Asn Leu Ile Asp Ser Ile Lys Thr
```

| | | | |
|---|---|---|---|
| Pro | His Thr Glu Leu Gln Lys Ile Thr Asp His Val Leu Lys Gly Thr | | |
| 945 | 950 | 955 | 960 |
| Thr Ser Leu Ala Asn His Thr Asn Glu Leu Leu Gly Leu Gly Asp Glu | | | |
| | 965 | 970 | 975 |
| Ser Leu Cys Asn Leu Glu Thr Thr Ile Glu Asp Thr Ser Leu Val Lys | | | |
| | 980 | 985 | 990 |
| Leu Glu Thr Thr Gly Asp Thr Pro Ser Lys Arg Glu Leu Pro Ala Thr | | | |
| | 995 | 1000 | 1005 |
| Pro Ser Trp Thr Arg Asp Ser Ser Leu Ile Lys Glu Thr Thr Asn Leu | | | |
| | 1010 | 1015 | 1020 |
| Asn Leu Asp Ser Asp Lys Lys Phe Val Arg Glu Thr Tyr Thr Ser Ser | | | |
| 1025 | 1030 | 1035 | 1040 |
| Asn Gln Thr Asn Glu Pro Asp Val Tyr Asp Lys Pro Ser Asn Ser Ser | | | |
| | 1045 | 1050 | 1055 |
| Arg Thr Ser Leu Leu Arg Ser Ser Arg Ser Ala Tyr Ser Lys Met Lys | | | |
| | 1060 | 1065 | 1070 |
| Arg | | | |

<210> SEQ ID NO 7
<211> LENGTH: 3709
<212> TYPE: DNA
<213> ORGANISM: Drosophila melanogaster

<400> SEQUENCE: 7

| | | | | | |
|---|---|---|---|---|---|
| ttttttttc | agggtgccgt | gttgcggtca | cactatttgc | gcattatttt | aaaattgaac | 60 |
| ggacaactga | agacgctgct | tctctctgtt | ctcattggaa | atagtgcgaa | aattggtttt | 120 |
| ccacgccagc | cttctgtaaa | tagtagttac | agttatcagc | attcggctcg | gtggaaggtg | 180 |
| aagcacaagg | atttccagga | atcaaacaca | cacacacacg | cataccgata | cacgcgacag | 240 |
| gcgtcatttt | ttggactgta | cgcgctaaaa | ccacaattaa | ttgtttcaat | tgatcaatat | 300 |
| ggacatatct | ggtgggaata | cgtcgcgcca | gccccaaaag | aagtccaacc | aaaacatcca | 360 |
| ggtgtatgtg | cgcgtcagac | cccttaattc | tcgggaacgt | tgcatccgct | cggccgaagt | 420 |
| cgtggatgtg | gtcggaccac | gggaagtggt | caccgccac | acgctggact | ccaagctcac | 480 |
| caagaagttc | acctttgacc | gcagttttgg | ccccgagtcc | aagcagtgcg | atgtctactc | 540 |
| cgtcgtggtg | tctccgctga | tcgaggaggt | cctcaatggc | tataactgca | cggtgtttgc | 600 |
| ttatggccag | acgggcacag | ggaagaccca | caccatggtg | ggcaacgaga | ctgccgaact | 660 |
| gaaatcctcc | tgggaagatg | actctgcat | tggcatcata | ccgcgcgctc | tgagtcacct | 720 |
| tttcgatgag | ctgcgcatga | tggaggtgga | gtacactatg | cgcatttcct | acttggaact | 780 |
| gtacaatgag | gagctgtgcg | atctactgtc | caccgatgac | accaccaaga | tacgcatttt | 840 |
| cgatgacagc | accaagaagg | gatcggtgat | tatccagggc | ctggaggaga | taccagtgca | 900 |
| cagcaaggat | gatgtgtaca | agctgctgga | gaagggaaag | gagcgtcgca | aaacagccac | 960 |
| tacgctgatg | aatgcacagt | cctcacgctc | ccacactgta | ttttctatag | ttgtgcacat | 1020 |
| cagggagaat | ggcatcgaag | gagaggacat | gctgaaaatc | ggtaaactga | atctggtgga | 1080 |
| tctggcgggc | agtgaaaatg | tttccaaggc | tgggaatgaa | aagggaatac | gtgtgcggga | 1140 |
| aacagtaaac | atcaatcaga | gcctcttgac | tctcggtaga | gtaattaccg | ctttggtcga | 1200 |
| tcgcgctcct | cacgttccat | atcgtgaatc | aaagctgact | agactgctgc | aagaatctct | 1260 |
| gggtggcagg | accaagacct | ccatcatagc | caccatatcg | ccgggccaca | aggacatcga | 1320 |

-continued

| | | | | | |
|---|---|---|---|---|---|
| ggagaccctg | agcactttag | agtacgctca | tcgcgccaag | aacattcaaa | acaagcccga | 1380 |
| agtcaatcag | aagctgacca | aaaagactgt | gctcaaggaa | tacaccgaag | aaatcgacaa | 1440 |
| gcttaaaaga | gatcttatgg | cggccaggga | caagaatggc | atctatttgg | ccgaggaaac | 1500 |
| ctacggggag | ataactttga | agttagaatc | ccagaaccgc | gagcttaacg | agaaaatgct | 1560 |
| gctgctcaag | gctttgaagg | acgaactcca | gaacaaggag | aagatcttca | gtgaggtgag | 1620 |
| catgagtctt | gtggagaaaa | cgcaggagct | gaaaaagacc | gaggagaacc | tactgaacac | 1680 |
| gaagggtact | ttgctcctga | ccaagaaagt | gctgaccaag | accaagcgac | gatacaagga | 1740 |
| aaaaaaggag | ttggtggcct | cgcatatgaa | aacggagcag | gttttgacca | cacaggctca | 1800 |
| ggagatccta | gccgctgctg | atctggccac | tgatgatact | catcagctgc | acggaaccat | 1860 |
| cgaaagaagg | cgtgagttgg | atgagaagat | tcgccgatct | tgcgatcagt | tcaaagatcg | 1920 |
| tatgcaggat | aatttggaaa | tgatcggtgg | cagcctgaac | ttgtatcagg | atcagcaggc | 1980 |
| agccctcaag | gagcagctaa | gccaggaaat | ggtaaactcg | agctatgtga | gccaacgcct | 2040 |
| tgcactaaat | tccagcaaaa | gcatcgaaat | gcttaaggga | atgtgtgccc | aatcgctaca | 2100 |
| ggatcagacc | aacctccata | ataagttaat | aggagaagtc | atgaagatca | gcgatcagca | 2160 |
| ctctcaggca | tttgtcgcca | agctgatgga | gcagatgcag | cagcaacagc | ttttgatgag | 2220 |
| caaagaaatt | cagactaacc | tgcaggtgat | cgaggaaaac | aaccagcggc | acaaagccat | 2280 |
| gctggactct | atgcaggaaa | agttcgccac | cataattgac | agcagcttac | agtctgtgga | 2340 |
| agaacatgcg | aagcaaatgc | acaagaagtt | ggagcagctc | ggggcaatga | gtttgccaga | 2400 |
| tgcggaggaa | ctgcagaatc | ttcaagagga | gttggcgaat | gaacgagctc | tggcgcagca | 2460 |
| ggaggatgct | ctccttgagt | ccatgatgat | gcagatggaa | cagatcaaga | acttgcggtc | 2520 |
| caaaaatagc | atcagcatgt | ccgtacatct | taataagatg | gaggagagtc | gactgacgag | 2580 |
| aaatcatcgc | atcgatgata | ttaagtctgg | tatccaagac | taccaaaagt | tgggcataga | 2640 |
| agcttcccaa | tccgcacaag | cggagctcac | cagccaaatg | gaggcgggaa | tgctttgtct | 2700 |
| ggaccaaggc | gttgccaact | gttcgatgct | tcaggtgcac | atgaagaatc | tcaaccagaa | 2760 |
| atacgaaaag | gaaacaaatg | agaatgttgg | ttccgttcga | gtgcaccaca | atcaggtgga | 2820 |
| aattatttgc | caagagagca | agcagcagct | tgaggcggtg | caggagaaaa | ccgaagttaa | 2880 |
| cttggaacag | atggtggatg | caaggcagca | gcttatcacc | gaggacagac | agcgattcat | 2940 |
| aggccatgcc | actgtagcca | ctgatcttgt | ccaagagtcg | aaccggcagt | tctcggagca | 3000 |
| tgctgaacac | caacggcagc | agctgcaaat | ttgcgagcaa | gagcttgtac | gcttccaaca | 3060 |
| gtcggagttg | aaaacgtacg | ccccaactgg | gaccacgccc | tccaaaaggg | atttcgttta | 3120 |
| tccgcgcacc | ctcgtggcca | cgtcgccaca | tcaggaaatt | gtgaggcgct | atcgccaaga | 3180 |
| gcaggactgg | tcagatctgg | acaccacggc | cactatagat | gagtgcagcg | agggtgagca | 3240 |
| tgacgactcc | atgcattccg | tccaggagct | gtccgaaact | gaaaccataa | tgaactccac | 3300 |
| gcccattgag | cccgtggatg | gtgtcaccgt | gaagcgtggg | tgcggcacca | cccgcaattc | 3360 |
| caattcgaac | gccctaaagc | cacccgtagc | tactggtgga | aaacgcagca | gctcgttgtc | 3420 |
| acgttccctg | acacccagta | aaacgtcacc | tcgaggttct | cccgccttcg | tcaggcacaa | 3480 |
| caaagaaaac | gtagcctgat | tgcattcgat | gacagtagta | gtctccccctt | cccagtaacc | 3540 |
| cgtttatgtt | agtggatttc | ggatcgctgt | gtttgtttgg | ctcttctgga | tattcatttt | 3600 |
| atctgtatat | caatctttgg | aatttcgtac | atttattatt | taaataaact | cagtatgcta | 3660 | tgtaaagtta aaaaaaaaaa aaaaaaaaaa aaaaaaaaaa aaaaaaaaa      3709

<210> SEQ ID NO 8
<211> LENGTH: 1066
<212> TYPE: PRT
<213> ORGANISM: Drosophila melanogaster

<400> SEQUENCE: 8

```
Met Asp Ile Ser Gly Gly Asn Thr Ser Arg Gln Pro Gln Lys Lys Ser
 1               5                  10                  15

Asn Gln Asn Ile Gln Val Tyr Val Arg Val Arg Pro Leu Asn Ser Arg
            20                  25                  30

Glu Arg Cys Ile Arg Ser Ala Glu Val Val Asp Val Val Gly Pro Arg
        35                  40                  45

Glu Val Val Thr Arg His Thr Leu Asp Ser Lys Leu Thr Lys Lys Phe
 50                  55                  60

Thr Phe Asp Arg Ser Phe Gly Pro Glu Ser Lys Gln Cys Asp Val Tyr
 65                  70                  75                  80

Ser Val Val Val Ser Pro Leu Ile Glu Val Leu Asn Gly Tyr Asn
                85                  90                  95

Cys Thr Val Phe Ala Tyr Gly Gln Thr Gly Thr Gly Lys Thr His Thr
            100                 105                 110

Met Val Gly Asn Glu Thr Ala Glu Leu Lys Ser Ser Trp Glu Asp Asp
            115                 120                 125

Ser Asp Ile Gly Ile Ile Pro Arg Ala Leu Ser His Leu Phe Asp Glu
        130                 135                 140

Leu Arg Met Met Glu Val Glu Tyr Thr Met Arg Ile Ser Tyr Leu Glu
145                 150                 155                 160

Leu Tyr Asn Glu Glu Leu Cys Asp Leu Leu Ser Thr Asp Thr Thr
                165                 170                 175

Lys Ile Arg Ile Phe Asp Asp Ser Thr Lys Lys Gly Ser Val Ile Ile
            180                 185                 190

Gln Gly Leu Glu Glu Ile Pro Val His Ser Lys Asp Asp Val Tyr Lys
        195                 200                 205

Leu Leu Glu Lys Gly Lys Glu Arg Arg Lys Thr Ala Thr Thr Leu Met
210                 215                 220

Asn Ala Gln Ser Ser Arg Ser His Thr Val Phe Ser Ile Val Val His
225                 230                 235                 240

Ile Arg Glu Asn Gly Ile Glu Gly Glu Asp Met Leu Lys Ile Gly Lys
                245                 250                 255

Leu Asn Leu Val Asp Leu Ala Gly Ser Glu Asn Val Ser Lys Ala Gly
            260                 265                 270

Asn Glu Lys Gly Ile Arg Val Arg Glu Thr Val Asn Ile Asn Gln Ser
        275                 280                 285

Leu Leu Thr Leu Gly Arg Val Ile Thr Ala Leu Val Asp Arg Ala Pro
    290                 295                 300

His Val Pro Tyr Arg Glu Ser Lys Leu Thr Arg Leu Leu Gln Glu Ser
305                 310                 315                 320

Leu Gly Gly Arg Thr Lys Thr Ser Ile Ile Ala Thr Ile Ser Pro Gly
                325                 330                 335

His Lys Asp Ile Glu Glu Thr Leu Ser Thr Leu Glu Tyr Ala His Arg
            340                 345                 350

Ala Lys Asn Ile Gln Asn Lys Pro Glu Val Asn Gln Lys Leu Thr Lys
        355                 360                 365
```

-continued

```
Lys Thr Val Leu Lys Glu Tyr Thr Glu Ile Asp Lys Leu Lys Arg
    370                 375                 380

Asp Leu Met Ala Ala Arg Asp Lys Asn Gly Ile Tyr Leu Ala Glu Glu
385                 390                 395                 400

Thr Tyr Gly Glu Ile Thr Leu Lys Leu Glu Ser Gln Asn Arg Glu Leu
                405                 410                 415

Asn Glu Lys Met Leu Leu Leu Lys Ala Leu Lys Asp Glu Leu Gln Asn
            420                 425                 430

Lys Glu Lys Ile Phe Ser Glu Val Ser Met Ser Leu Val Glu Lys Thr
            435                 440                 445

Gln Glu Leu Lys Lys Thr Glu Glu Asn Leu Leu Asn Thr Lys Gly Thr
        450                 455                 460

Leu Leu Leu Thr Lys Lys Val Leu Thr Lys Thr Lys Arg Arg Tyr Lys
465                 470                 475                 480

Glu Lys Lys Glu Leu Val Ala Ser His Met Lys Thr Glu Gln Val Leu
                485                 490                 495

Thr Thr Gln Ala Gln Glu Ile Leu Ala Ala Ala Asp Leu Ala Thr Asp
            500                 505                 510

Asp Thr His Gln Leu His Gly Thr Ile Glu Arg Arg Arg Glu Leu Asp
        515                 520                 525

Glu Lys Ile Arg Arg Ser Cys Asp Gln Phe Lys Asp Arg Met Gln Asp
    530                 535                 540

Asn Leu Glu Met Ile Gly Gly Ser Leu Asn Leu Tyr Gln Asp Gln Gln
545                 550                 555                 560

Ala Ala Leu Lys Glu Gln Leu Ser Gln Glu Met Val Asn Ser Ser Tyr
                565                 570                 575

Val Ser Gln Arg Leu Ala Leu Asn Ser Ser Lys Ser Ile Glu Met Leu
            580                 585                 590

Lys Glu Met Cys Ala Gln Ser Leu Gln Asp Gln Thr Asn Leu His Asn
        595                 600                 605

Lys Leu Ile Gly Glu Val Met Lys Ile Ser Asp Gln His Ser Gln Ala
    610                 615                 620

Phe Val Ala Lys Leu Met Glu Gln Met Gln Gln Gln Leu Leu Met
625                 630                 635                 640

Ser Lys Glu Ile Gln Thr Asn Leu Gln Val Ile Glu Glu Asn Asn Gln
                645                 650                 655

Arg His Lys Ala Met Leu Asp Ser Met Gln Glu Lys Phe Ala Thr Ile
            660                 665                 670

Ile Asp Ser Ser Leu Gln Ser Val Glu Glu His Ala Lys Gln Met His
        675                 680                 685

Lys Lys Leu Glu Gln Leu Gly Ala Met Ser Leu Pro Asp Ala Glu Glu
    690                 695                 700

Leu Gln Asn Leu Gln Glu Glu Leu Ala Asn Glu Arg Ala Leu Ala Gln
705                 710                 715                 720

Gln Glu Asp Ala Leu Leu Glu Ser Met Met Gln Met Glu Gln Ile
                725                 730                 735

Lys Asn Leu Arg Ser Lys Asn Ser Ile Ser Met Ser Val His Leu Asn
            740                 745                 750

Lys Met Glu Glu Ser Arg Leu Thr Arg Asn His Arg Ile Asp Asp Ile
        755                 760                 765

Lys Ser Gly Ile Gln Asp Tyr Gln Lys Leu Gly Ile Glu Ala Ser Gln
    770                 775                 780

Ser Ala Gln Ala Glu Leu Thr Ser Gln Met Glu Ala Gly Met Leu Cys
```

```
                785                 790                 795                 800
Leu Asp Gln Gly Val Ala Asn Cys Ser Met Leu Gln Val His Met Lys
                805                 810                 815
Asn Leu Asn Gln Lys Tyr Glu Lys Glu Thr Asn Glu Asn Val Gly Ser
                820                 825                 830
Val Arg Val His His Asn Gln Val Glu Ile Ile Cys Gln Glu Ser Lys
                835                 840                 845
Gln Gln Leu Glu Ala Val Gln Glu Lys Thr Glu Val Asn Leu Glu Gln
                850                 855                 860
Met Val Asp Ala Arg Gln Leu Ile Thr Glu Asp Arg Gln Arg Phe
865                 870                 875                 880
Ile Gly His Ala Thr Val Ala Thr Asp Leu Val Gln Glu Ser Asn Arg
                885                 890                 895
Gln Phe Ser Glu His Ala Glu His Gln Arg Gln Gln Leu Gln Ile Cys
                900                 905                 910
Glu Gln Glu Leu Val Arg Phe Gln Gln Ser Glu Leu Lys Thr Tyr Ala
                915                 920                 925
Pro Thr Gly Thr Thr Pro Ser Lys Arg Asp Phe Val Tyr Pro Arg Thr
                930                 935                 940
Leu Val Ala Thr Ser Pro His Gln Glu Ile Val Arg Arg Tyr Arg Gln
945                 950                 955                 960
Glu Gln Asp Trp Ser Asp Leu Asp Thr Thr Ala Thr Ile Asp Glu Cys
                965                 970                 975
Ser Glu Gly Glu His Asp Asp Ser Met His Ser Val Gln Glu Leu Ser
                980                 985                 990
Glu Thr Glu Thr Ile Met Asn Ser Thr Pro Ile Glu Pro Val Asp Gly
                995                 1000                1005
Val Thr Val Lys Arg Gly Cys Gly Thr Thr Arg Asn Ser Asn Ser Asn
    1010                1015                1020
Ala Leu Lys Pro Pro Val Ala Thr Gly Gly Lys Arg Ser Ser Ser Leu
1025                1030                1035                1040
Ser Arg Ser Leu Thr Pro Ser Lys Thr Ser Pro Arg Gly Ser Pro Ala
                1045                1050                1055
Phe Val Arg His Asn Lys Glu Asn Val Ala
                1060                1065
```

<210> SEQ ID NO 9
<211> LENGTH: 3741
<212> TYPE: DNA
<213> ORGANISM: H.sapiens

<400> SEQUENCE: 9

```
gaattccgtc atggcgtcgc agccaaattc gtctgcgaag aagaaagagg agaaggggaa    60
gaacatccag gtggtggtga gatgcagacc atttaatttg gcagagcgga aagctagcgc   120
ccattcaata gtagaatgtg atcctgtacg aaaagaagtt agtgtacgaa ctggaggatt   180
ggctgacaag agctcaagga aaacatacac ttttgatatg gtgtttggag catctactaa   240
acagattgat gtttaccgaa gtgttgtttg tccaattctg gatgaagtta ttatgggcta   300
taattgcact atctttgcgt atggccaaac tggcactgga aaacttttta caatggaagg   360
tgaaaggtca cctaatgaag agtatacctg gaagaggat cccttggctg gtataattcc   420
acgtaccctt catcaaattt ttgagaaact tactgataat ggtactgaat ttcagtcaa   480
agtgtctctg ttggagatct ataatgaaga gcttttggat cttcttaatc catcatctga   540
```

-continued

```
tgtttctgag agactacaga tgtttgatga tccccgtaac aagagaggag tgataattaa      600
aggtttagaa gaaattacag tacacaacaa ggatgaagtc tatcaaattt tagaaagggg      660
ggcagcaaaa aggacaactg cagctactct gatgaatgca tactctagtc gttcccactc      720
agttttctct gttacaatac atatgaaaga aactacgatt gatggagaag agcttgttaa      780
aatcggaaaa ttgaacttgg ttgatcttgc aggaagtgaa acattggcc gttctggagc       840 tgttgataag agagctcggg aagctggaaa tataaatcaa tccctgttga ctttgggaag      900
ggtcattact gcccttgtag aaagaacacc tcatgttcct tatcgagaat ctaaactaac      960
tagaatcctc caggattctc ttggagggcg tacaagaaca tctataattg caacaatttc     1020
tcctgcatct ctcaatcttg aggaaactct gagtacattg gaatatgctc atagagcaaa     1080
gaacatattg aataagcctg aagtgaatca gaaactcacc aaaaaagctc ttattaagga     1140
gtatacggag gagatagaac gtttaaaacg agatcttgct gcagcccgtg agaaaaatgg     1200
agtgtatatt tctgaagaaa attttagagt catgagtgga aaattaactg ttcaagaaga     1260
gcagattgta gaattgattg aaaaaattgg tgctgttgag gaggagctga ataggggttac    1320 agagttgttt atggataata aaaatgaact tgaccagtgt aaatctgacc tgcaaaataa     1380
aacacaagaa cttgaaacca ctcaaaaaca tttgcaagaa actaaattac aacttgttaa     1440
agaagaatat atcacatcag ctttggaaag tactgaggag aaacttcatg atgctgccag     1500
caagctgctt aacacagttg aagaaactac aaaagatgta tctggtctcc attccaaact     1560
ggatcgtaag aaggcagttg accaacacaa tgcagaagct caggatattt ttggcaaaaa     1620
cctgaatagt ctgtttaata atatggaaga attaattaag gatggcagct caaagcaaaa     1680
ggccatgcta gaagtacata agaccttatt tggtaatctg ctgtcttcca gtgtctctgc     1740
attagatacc attactacag tagcacttgg atctctcaca tctattccag aaaatgtgtc     1800
tactcatgtt tctcagattt ttaatatgat actaaaagaa caatcattag cagcagaaag     1860
taaaactgta ctacaggaat tgattaatgt actcaagact gatcttctaa gttcactgga     1920
aatgatttta tccccaactg tggtgtctat actgaaaatc aatagtcaac taaagcatat     1980
tttcaagact tcattgacag tggccgataa gatagaagat caaaaaaaaa ggaactcaga     2040
tggctttctc agtatactgt gtaacaatct acatgaacta caagaaaata ccatttgttc     2100
cttggttgag tcacaaaagc aatgtggaaa cctaactgaa gacctgaaga caataaagca     2160
gacccattcc caggaacttt gcaagttaat gaatctttgg acagagagat tctgtgcttt     2220
ggaggaaaag tgtgaaaata tacagaaacc acttagtagt gtccaggaaa atatacagca     2280
gaaatctaag gatatagtca acaaaatgac ttttcacagt caaaaatttt gtgctgattc     2340
tgatggcttc tcacaggaac tcagaaattt taaccaagaa ggtacaaaat tggttgaaga     2400
atctgtgaaa cactctgata aactcaatgg caacctggaa aaaatatctc aagagactga     2460
acagagatgt gaatctctga acacaagaac agtttatttt tctgaacagt gggtatcttc     2520
cttaaatgaa agggaacagg aacttcacaa cttattggag gttgtaagcc aatgttgtga     2580
ggcttcaagt tcagacatca ctgagaaatc agatggacgt aaggcagctc atgagaaaca     2640
gcataacatt tttcttgatc agatgactat tgatgaagat aaattgatag cacaaaatct     2700
agaacttaat gaaaccataa aaattggttt gactaagctt aattgctttc tggaacagga     2760
tctgaaactg gatatcccaa caggtacgac accacagagg aaaagttatt tatacccatc     2820
aacactggta agaactgaac cacgtgaaca tctccttgat cagctgaaaa ggaaacagcc     2880
tgagctgtta atgatgctaa actgttcaga aaacaacaaa gaagagacaa ttccggatgt     2940
```

-continued

```
ggatgtagaa gaggcagttc tgggcagta tactgaagaa cctctaagtc aagagccatc    3000
tgtagatgct ggtgtggatt gttcatcaat tggcggggtt ccattttcc agcataaaaa    3060 atcacatgga aagacaaag aaaacagagg cattaacaca ctggagaggt ctaaagtgga    3120
agaaactaca gagcacttgg ttacaaagag cagattacct ctgcgagccc agatcaacct    3180
ttaattcact tggggttgg caattttatt tttaaagaaa aacttaaaaa taaaacctga    3240
aaccccagaa cttgagcctt gtgtatagat tttaaagaa tatatatatc agccgggcgc    3300
gtggctctag ctgtaatccc agctaactt ggaggctgag gcgggtggat tgcttgagcc    3360
caggagtttg agaccagcct ggccaacgtg cgctaaaacc ttcgtctctg ttaaaaatta    3420
gccgggcgtg gtgggcacac tcctgtaatc ccagctactg ggaggctga ggcacgagaa    3480 tcacttgaac ccagaagcgg ggttgcagtg agccaaaggt acaccactac actccagcct    3540
gggcaacaga gcaagactcg gtctcaaaaa taaaatttaa aaaagatata aggcagtact    3600
gtaaattcag ttgaattttg atatctaccc atttttctgt catccctata gttcactttg    3660
tattaaattg ggttcattt gggatttgca atgtaaatac gtatttctag ttttcatata    3720
aagtagttct tttaggaatt c                                              3741
```

```
<210> SEQ ID NO 10
<211> LENGTH: 1057
<212> TYPE: PRT
<213> ORGANISM: H.sapiens

<400> SEQUENCE: 10
```

```
Met Ala Ser Gln Pro Asn Ser Ser Ala Lys Lys Glu Glu Lys Gly
 1               5                  10                  15

Lys Asn Ile Gln Val Val Arg Cys Arg Pro Phe Asn Leu Ala Glu
             20                  25                  30

Arg Lys Ala Ser Ala His Ser Ile Val Glu Cys Asp Pro Val Arg Lys
         35                  40                  45

Glu Val Ser Val Arg Thr Gly Gly Leu Ala Asp Lys Ser Ser Arg Lys
     50                  55                  60

Thr Tyr Thr Phe Asp Met Val Phe Gly Ala Ser Thr Lys Gln Ile Asp
 65                  70                  75                  80

Val Tyr Arg Ser Val Val Cys Pro Ile Leu Asp Glu Val Ile Met Gly
                 85                  90                  95

Tyr Asn Cys Thr Ile Phe Ala Tyr Gly Gln Thr Gly Thr Gly Lys Thr
            100                 105                 110

Phe Thr Met Glu Gly Glu Arg Ser Pro Asn Glu Glu Tyr Thr Trp Glu
        115                 120                 125

Glu Asp Pro Leu Ala Gly Ile Ile Pro Arg Thr Leu His Gln Ile Phe
    130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
                165                 170                 175

Asp Val Ser Glu Arg Leu Gln Met Phe Asp Asp Pro Arg Asn Lys Arg
            180                 185                 190

Gly Val Ile Ile Lys Gly Leu Glu Glu Ile Thr Val His Asn Lys Asp
        195                 200                 205

Glu Val Tyr Gln Ile Leu Glu Lys Gly Ala Ala Lys Arg Thr Thr Ala
    210                 215                 220
```

-continued

```
Ala Thr Leu Met Asn Ala Tyr Ser Ser Arg Ser His Ser Val Phe Ser
225                 230                 235                 240

Val Thr Ile His Met Lys Glu Thr Thr Ile Asp Gly Glu Glu Leu Val
                245                 250                 255

Lys Ile Gly Lys Leu Asn Leu Val Asp Leu Ala Gly Ser Glu Asn Ile
            260                 265                 270

Gly Arg Ser Gly Ala Val Asp Lys Arg Ala Arg Glu Ala Gly Asn Ile
        275                 280                 285

Asn Gln Ser Leu Leu Thr Leu Gly Arg Val Ile Thr Ala Leu Val Glu
    290                 295                 300

Arg Thr Pro His Val Pro Tyr Arg Glu Ser Lys Leu Thr Arg Ile Leu
305                 310                 315                 320

Gln Asp Ser Leu Gly Gly Arg Thr Arg Thr Ser Ile Ile Ala Thr Ile
                325                 330                 335

Ser Pro Ala Ser Leu Asn Leu Glu Glu Thr Leu Ser Thr Leu Glu Tyr
            340                 345                 350

Ala His Arg Ala Lys Asn Ile Leu Asn Lys Pro Glu Val Asn Gln Lys
        355                 360                 365

Leu Thr Lys Lys Ala Leu Ile Lys Glu Tyr Thr Glu Glu Ile Glu Arg
    370                 375                 380

Leu Lys Arg Asp Leu Ala Ala Arg Glu Lys Asn Gly Val Tyr Ile
385                 390                 395                 400

Ser Glu Glu Asn Phe Arg Val Met Ser Gly Lys Leu Thr Val Gln Glu
                405                 410                 415

Glu Gln Ile Val Glu Leu Ile Glu Lys Ile Gly Ala Val Glu Glu Glu
            420                 425                 430

Leu Asn Arg Val Thr Glu Leu Phe Met Asp Asn Lys Asn Glu Leu Asp
        435                 440                 445

Gln Cys Lys Ser Asp Leu Gln Asn Lys Thr Gln Glu Leu Glu Thr Thr
    450                 455                 460

Gln Lys His Leu Gln Glu Thr Lys Leu Gln Leu Val Lys Glu Glu Tyr
465                 470                 475                 480

Ile Thr Ser Ala Leu Glu Ser Thr Glu Glu Lys Leu His Asp Ala Ala
                485                 490                 495

Ser Lys Leu Leu Asn Thr Val Glu Glu Thr Thr Lys Asp Val Ser Gly
            500                 505                 510

Leu His Ser Lys Leu Asp Arg Lys Lys Ala Val Asp Gln His Asn Ala
        515                 520                 525

Glu Ala Gln Asp Ile Phe Gly Lys Asn Leu Asn Ser Leu Phe Asn Asn
    530                 535                 540

Met Glu Glu Leu Ile Lys Asp Gly Ser Ser Lys Gln Lys Ala Met Leu
545                 550                 555                 560

Glu Val His Lys Thr Leu Phe Gly Asn Leu Leu Ser Ser Ser Val Ser
                565                 570                 575

Ala Leu Asp Thr Ile Thr Thr Val Ala Leu Gly Ser Leu Thr Ser Ile
            580                 585                 590

Pro Glu Asn Val Ser Thr His Val Ser Gln Ile Phe Asn Met Ile Leu
        595                 600                 605

Lys Glu Gln Ser Leu Ala Ala Glu Ser Lys Thr Val Leu Gln Glu Leu
    610                 615                 620

Ile Asn Val Leu Lys Thr Asp Leu Leu Ser Ser Leu Glu Met Ile Leu
625                 630                 635                 640

Ser Pro Thr Val Val Ser Ile Leu Lys Ile Asn Ser Gln Leu Lys His
```

```
                    645                 650                 655
Ile Phe Lys Thr Ser Leu Thr Val Ala Asp Lys Ile Glu Asp Gln Lys
            660                 665                 670

Lys Arg Asn Ser Asp Gly Phe Leu Ser Ile Leu Cys Asn Asn Leu His
            675                 680                 685

Glu Leu Gln Glu Asn Thr Ile Cys Ser Leu Val Glu Ser Gln Lys Gln
            690                 695                 700

Cys Gly Asn Leu Thr Glu Asp Leu Lys Thr Ile Lys Gln Thr His Ser
705                 710                 715                 720

Gln Glu Leu Cys Lys Leu Met Asn Leu Trp Thr Glu Arg Phe Cys Ala
                    725                 730                 735

Leu Glu Glu Lys Cys Glu Asn Ile Gln Lys Pro Leu Ser Ser Val Gln
                740                 745                 750

Glu Asn Ile Gln Gln Lys Ser Lys Asp Ile Val Asn Lys Met Thr Phe
                755                 760                 765

His Ser Gln Lys Phe Cys Ala Asp Ser Asp Gly Phe Ser Gln Glu Leu
                770                 775                 780

Arg Asn Phe Asn Gln Glu Gly Thr Lys Leu Val Glu Glu Ser Val Lys
785                 790                 795                 800

His Ser Asp Lys Leu Asn Gly Asn Leu Glu Lys Ile Ser Gln Glu Thr
                805                 810                 815

Glu Gln Arg Cys Glu Ser Leu Asn Thr Arg Thr Val Tyr Phe Ser Glu
                820                 825                 830

Gln Trp Val Ser Ser Leu Asn Glu Arg Glu Gln Glu Leu His Asn Leu
                835                 840                 845

Leu Glu Val Val Ser Gln Cys Cys Glu Ala Ser Ser Ser Asp Ile Thr
                850                 855                 860

Glu Lys Ser Asp Gly Arg Lys Ala Ala His Glu Lys Gln His Asn Ile
865                 870                 875                 880

Phe Leu Asp Gln Met Thr Ile Asp Glu Asp Lys Leu Ile Ala Gln Asn
                    885                 890                 895

Leu Glu Leu Asn Glu Thr Ile Lys Ile Gly Leu Thr Lys Leu Asn Cys
                900                 905                 910

Phe Leu Glu Gln Asp Leu Lys Leu Asp Ile Pro Thr Gly Thr Thr Pro
                915                 920                 925

Gln Arg Lys Ser Tyr Leu Tyr Pro Ser Thr Leu Val Arg Thr Glu Pro
930                 935                 940

Arg Glu His Leu Leu Asp Gln Leu Lys Arg Lys Gln Pro Glu Leu Leu
945                 950                 955                 960

Met Met Leu Asn Cys Ser Glu Asn Asn Lys Glu Glu Thr Ile Pro Asp
                965                 970                 975

Val Asp Val Glu Glu Ala Val Leu Gly Gln Tyr Thr Glu Glu Pro Leu
                980                 985                 990

Ser Gln Glu Pro Ser Val Asp Ala Gly Val Asp Cys Ser Ser Ile Gly
                995                 1000                1005

Gly Val Pro Phe Phe Gln His Lys Lys Ser His Gly Lys Asp Lys Glu
            1010                1015                1020

Asn Arg Gly Ile Asn Thr Leu Glu Arg Ser Lys Val Glu Glu Thr Thr
1025                1030                1035                1040

Glu His Leu Val Thr Lys Ser Arg Leu Pro Leu Arg Ala Gln Ile Asn
                1045                1050                1055

Leu
```